(12) United States Patent
Racz et al.

(10) Patent No.: US 10,448,972 B2
(45) Date of Patent: Oct. 22, 2019

(54) DEPLOYMENT DEVICES AND RELATED ASSEMBLIES AND METHODS

(71) Applicant: Custom Medical Applications Inc., Farmers Branch, TX (US)

(72) Inventors: N. Sandor Racz, Farmers Branch, TX (US); James Shoemake, Plano, TX (US); Kevin Dean Joiner, Dallas, TX (US)

(73) Assignee: Custom Medical Applications Inc., Farmers Branch, TX (US)

( * ) Notice: Subject to any disclaimer, the term of this patent is extended or adjusted under 35 U.S.C. 154(b) by 0 days.

(21) Appl. No.: 15/759,492

(22) PCT Filed: Sep. 15, 2016

(86) PCT No.: PCT/US2016/051988
§ 371 (c)(1),
(2) Date: Mar. 12, 2018

(87) PCT Pub. No.: WO2017/048992
PCT Pub. Date: Mar. 23, 2017

(65) Prior Publication Data
US 2019/0110811 A1    Apr. 18, 2019

Related U.S. Application Data

(60) Provisional application No. 62/218,988, filed on Sep. 15, 2015.

(51) Int. Cl.
*A61B 17/34* (2006.01)
*A61N 1/05* (2006.01)
(Continued)

(52) U.S. Cl.
CPC .......... *A61B 17/3468* (2013.01); *A61N 1/057* (2013.01); *A61N 1/0551* (2013.01);
(Continued)

(58) Field of Classification Search
CPC ................ A61N 1/056; A61N 1/0587; A61B 2017/22049; A61B 17/3468;
(Continued)

(56) References Cited

U.S. PATENT DOCUMENTS 3,397,699 A    8/1968  Kohl
4,374,527 A    2/1983  Iversen
(Continued)

FOREIGN PATENT DOCUMENTS

EP    0779080    6/1997
FR    0779080    3/1935
(Continued)

OTHER PUBLICATIONS

Notice of Reasons for Rejection in Korean Patent Application No. 10-2018-7010527 dated Jan. 25, 2019, 6 pages (W/Translation).
(Continued)

*Primary Examiner* — Christopher L Templeton
(74) *Attorney, Agent, or Firm* — TraskBritt

(57) ABSTRACT

Deployment devices include a locking mechanism configured to secure a medical device to the deployment device. Methods of operating a deployment device include securing a medical device positioned at least partially within at least one cannula of the deployment device with a locking mechanism and releasing the medical device and securing at least a portion of the at least one cannula of the deployment device with the locking mechanism.

9 Claims, 17 Drawing Sheets

(51) Int. Cl.
*A61B 10/00* (2006.01)
*A61M 5/14* (2006.01)
*A61B 17/00* (2006.01)

(52) U.S. Cl.
CPC ........ *A61N 1/0558* (2013.01); *A61B 10/0045* (2013.01); *A61B 2017/00469* (2013.01); *A61B 2017/347* (2013.01); *A61B 2017/3488* (2013.01); *A61M 5/14* (2013.01)

(58) Field of Classification Search
CPC ...... A61M 2025/09125; A61M 5/1418; A61M 25/02; A61M 25/0097; A61M 2025/024
See application file for complete search history.

(56) References Cited

U.S. PATENT DOCUMENTS

| | | | |
|---|---|---|---|
| 4,406,042 | A | 9/1983 | McPhee |
| 4,419,819 | A | 12/1983 | Dickhudt et al. |
| 4,913,164 | A | 4/1990 | Greene et al. |
| 5,238,007 | A | 8/1993 | Giele et al. |
| 5,344,439 | A | 9/1994 | Otten |
| 5,584,874 | A | 12/1996 | Rugland et al. |
| 5,658,309 | A * | 8/1997 | Berthiaume ...... A61M 25/0097 604/96.01 |
| 5,769,786 | A * | 6/1998 | Wiegel ................ A61M 25/09 600/372 |
| 6,358,256 | B1 | 3/2002 | Reinhardt |
| 6,473,654 | B1 | 10/2002 | Chinn |
| 6,517,573 | B1 | 2/2003 | Pollock et al. |
| 6,901,287 | B2 | 5/2005 | Davis et al. |
| 7,056,286 | B2 | 6/2006 | Ravenscroft et al. |
| 7,090,661 | B2 | 8/2006 | Morris et al. |
| D531,724 | S | 11/2006 | Gessert et al. |
| 7,270,650 | B2 | 9/2007 | Morris et al. |
| 7,509,169 | B2 | 3/2009 | Eigler et al. |
| 7,517,337 | B2 | 4/2009 | Morris et al. |
| 7,591,970 | B2 | 9/2009 | Olson |
| 7,731,132 | B2 | 6/2010 | Raines, Jr. |
| 7,753,889 | B2 | 7/2010 | Rosenberg |
| 7,811,251 | B2 | 10/2010 | Wenchell et al. |
| 7,890,186 | B2 | 2/2011 | Wardle et al. |
| 8,016,794 | B2 | 9/2011 | Rosenberg et al. |
| 8,016,813 | B2 | 9/2011 | Rosenberg et al. |
| 8,038,653 | B2 | 10/2011 | Rosenberg et al. |
| 8,118,749 | B2 | 2/2012 | White et al. |
| 8,142,401 | B2 | 3/2012 | Rosenberg |
| 8,192,402 | B2 | 6/2012 | Anderson et al. |
| 8,229,573 | B2 | 7/2012 | Chen et al. |
| 8,235,948 | B2 | 8/2012 | Rosenberg et al. |
| 8,295,948 | B2 | 10/2012 | Barker et al. |
| 8,298,281 | B2 | 10/2012 | Majercak et al. |
| 8,311,643 | B2 | 11/2012 | North |
| 8,333,687 | B2 | 12/2012 | Farnan et al. |
| 8,740,972 | B2 | 6/2014 | Roeder et al. |
| D709,753 | S | 7/2014 | Guala |
| D718,436 | S | 11/2014 | Redol |
| D785,793 | S | 5/2017 | Landanger |
| 10,105,224 | B2 | 10/2018 | Buchbinder et al. |
| 2001/0021824 | A1* | 9/2001 | Marsh ................ A61B 17/3401 604/164.09 |
| 2001/0037141 | A1 | 11/2001 | Yee et al. |
| 2002/0161341 | A1 | 10/2002 | Stinson et al. |
| 2003/0199961 | A1 | 10/2003 | Bjorklund et al. |
| 2005/0065589 | A1 | 3/2005 | Schneider et al. |
| 2005/0288604 | A1 | 12/2005 | Eigler et al. |
| 2008/0172118 | A1 | 7/2008 | Johnson et al. |
| 2008/0183257 | A1 | 7/2008 | Imran et al. |
| 2009/0105746 | A1 | 4/2009 | Spenser et al. |
| 2009/0112050 | A1 | 4/2009 | Farnan et al. |
| 2009/0248054 | A1 | 10/2009 | Sage et al. |
| 2010/0030311 | A1 | 2/2010 | Lazeroms et al. |
| 2010/0125249 | A1 | 5/2010 | Rosenberg et al. |
| 2010/0174296 | A1 | 7/2010 | Vakharia et al. |
| 2012/0035699 | A1 | 2/2012 | Hanse et al. |
| 2012/0071833 | A1 | 3/2012 | Hill et al. |
| 2012/0083742 | A1 | 4/2012 | Nelson |
| 2014/0188165 | A1 | 7/2014 | Sengun et al. |
| 2014/0276418 | A1 | 9/2014 | Nelson et al. |

FOREIGN PATENT DOCUMENTS

| | | |
|---|---|---|
| FR | 2742058 | 6/1997 |
| JP | 2007-532265 A | 11/2007 |
| JP | 2010-516436 A | 5/2010 |
| JP | 2011-500286 A | 1/2011 |
| WO | 2010085456 | 7/2010 |
| WO | 2013070490 A1 | 5/2013 |
| WO | 2015077796 A1 | 5/2015 |

OTHER PUBLICATIONS

European Partial Search Report for European Application No. 16847329.6, dated Mar. 1, 2019, 13 pages.
Notice of Reasons for Rejection for Japanese Patent Application No. 2018-525789, dated Oct. 15, 2018 (11 pages w/Eng Translation).
Written Opinion of the International Search Authority for International Application No. PCT/-US2016/51988 dated Dec. 20, 2106, 8 pages.
Written Opinion of the International Search Authority for International Application No. PCT/-US2016/51988 dated Dec. 20, 2016, 8 pages.
International Search Report for International Application No. PCT/2016/51988 dated Dec. 20, 2016, 3 pages.
Notice of Reasons for Rejection in Korean Patent Application No. 10-2018-7010527 dated May 31, 2019, 15 pages (W/Translation).
Notice of Reasons for Rejection in Japanese Patent Application No. 2018-525789 dispatched Apr. 11, 2019, 4 pages (W/Translation).
European Extended Search Report and Opinion for European Application No. 16847329.6, dated Jun. 7, 2019, 11 pages.

* cited by examiner

DEPLOYMENT DEVICES AND RELATED ASSEMBLIES AND METHODS

CROSS-REFERENCE TO RELATED APPLICATIONS

This application is a national phase entry under 35 U.S.C. § 371 of International Patent Application PCT/US2016/051988, filed Sep. 15, 2016, designating the United States of America and published in English as International Patent Publication WO 2017/048992 A8 on Mar. 23, 2017, which claims the benefit under Article 8 of the Patent Cooperation Treaty to U.S. Provisional Patent Application Ser. No. 62/218,988, filed Sep. 15, 2015, for "Deployment Devices and Related Assemblies and Methods," the disclosure of each of which is hereby incorporated herein in its entirety by this reference.

TECHNICAL FIELD

The disclosure relates generally to the field of medical devices and related methods. In particular, the disclosure relates to deployment devices that may be utilized to deploy another device, such as one or more anchor elements and/or anchor element assemblies, where such anchor elements may be utilized to retain at least a portion of a medical device (e.g., a medical therapy delivery device) within a subject and related methods.

BACKGROUND

Implantable medical devices (e.g., medical therapy delivery devices), such as catheters and leads, may be employed for a variety of therapeutic and diagnostic purposes. Controlled placement and retention of such therapy delivery elements in a subject is highly desirable as precise placement and retention should result in improved therapeutic efficacy and/or reduced side effects. However, the location of the delivery element may change in time. For example, as the subject moves, the location of an implanted delivery element may move or shift within the subject.

Anchors may be placed about the therapy delivery element and sutured to subcutaneous tissue of the subject in order to secure the position of a delivery region of the therapy delivery element (e.g., an infusion section or electrode of the delivery element) relative to a target location of the subject.

For example, U.S. Pat. No. 8,295,948 to Barker et al., the disclosure of which is hereby incorporated herein in its entirety by this reference, describes tubular anchors for use with implantable spinal cord stimulators. These lead anchors require that the lead or leads of the implantable spinal cord stimulator be threaded through multiple tubular members and the lead anchor secured to the subject's tissue with sutures. However, it would be advantageous to provide deployment devices for medical devices and medical device anchors and anchoring systems that enable a practitioner to reliably and repeatedly install such anchors (or other components) on a medical device, while simplifying the installment procedures.

BRIEF SUMMARY

Described are deployment devices, anchor elements, anchor element assemblies, methods of anchoring at least a portion of a medical device within a subject, and other related methods. Such deployment devices may be utilized to position and/or deploy one or more anchor elements within the subject on a medical device while at least a portion of the medical device is positioned within (e.g., resident in) the subject.

Disclosed is an anchor deployment device comprising at least one cannula configured to receive at least one anchor element on the at least one cannula and a medical device within the at least one cannula. The anchor deployment device is configured to selectively secure the medical device and a portion of the at least one cannula (e.g., during an anchor placement procedure within a subject).

Also disclosed is an anchor deployment device comprising at least one cannula configured to receive at least one anchor element on the at least one cannula and a medical device within the at least one cannula and a locking mechanism configured to secure the medical device to the anchor deployment device.

Further disclosed is a method of operating a deployment device. The method includes securing a medical device positioned at least partially within at least one cannula of the deployment device with a locking mechanism, releasing the medical device, and securing at least a portion of the at least one cannula of the deployment device with the locking mechanism.

In some embodiments, an anchor element assembly comprises at least one anchor element having a longitudinal axis. This anchor element includes at least one lobe section comprising at least one lobe configured to extend transversely or laterally from the longitudinal axis of the at least one anchor element when the at least one anchor element is in a deployed state and a lumen formed within the at least one anchor element configured to receive at least a portion of a medical device in the lumen. The anchor element assembly further comprises an anchor deployment device comprising at least one cannula configured to receive the at least one anchor element on the at least one cannula. The anchor deployment device is configured to secure the anchor deployment device to the at least a portion of the medical device.

In certain embodiments, an anchor element comprising at least one protrusion section comprises at least two circumferentially-spaced protrusions configured to extend transversely or laterally from a longitudinal axis of the anchor element when the anchor element is in a deployed state and a lumen formed within the anchor element configured to receive at least a portion of a medical device in the lumen. The anchor element is configured to be secured over the at least a portion of the medical device while the at least a portion of the medical device is positioned within a subject.

Also disclosed is an anchor deployment device assembly. The anchor deployment device assembly includes an anchor deployment device configured to position at least one anchor element on a medical device to secure a portion of the medical device within a subject and an anchor loading device comprising at least one post to receive the at least one anchor element. The anchor loading device is configured to transfer the at least one anchor element from the anchor loading device to the anchor deployment device when a force is applied to at least one of the anchor loading device or the anchor deployment device.

Also disclosed is a method of anchoring a medical device within a subject. The method includes positioning at least a portion of the medical device within the subject, securing the at least a portion of the medical device within a lumen of at least one anchor element, and deploying at least one protrusion of the at least one anchor element to extend transversely or laterally from a longitudinal axis of the at least one anchor element while the at least a portion of the medical device is positioned within the subject.

Also disclosed are medical device assemblies including such anchor elements and/or anchor element assemblies.

Also disclosed are methods of forming and utilizing anchor elements and anchor element assemblies according to the disclosure.

DETAILED DESCRIPTION

Illustrations presented herein are not necessarily meant to be actual views of any particular device, assembly, system, method, or components thereof, but are merely idealized representations, which are employed to describe embodiments of the disclosure. Additionally, elements common between figures may retain the same numerical designation.

Figure 1:
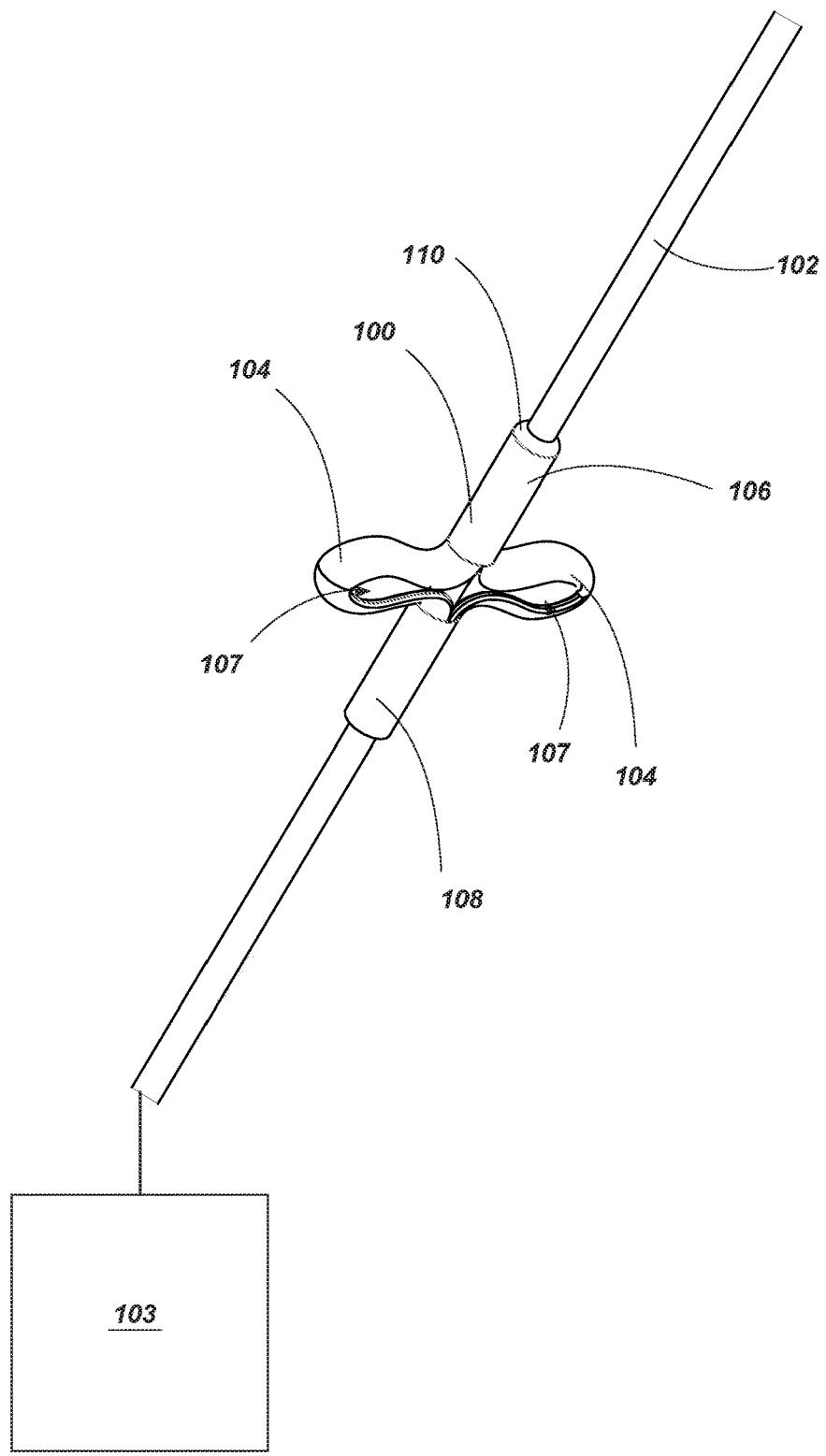
FIG. 1 depicts a medical device assembly including an anchor element positioned on a medical device in accordance with an embodiment of the disclosure.

FIG. 1 depicts a medical device assembly including an anchor element 100 positioned on a medical device 102 (e.g., a distal portion of the medical device 102). Such medical devices 102 may include a diagnostic device, a monitoring device, a therapeutic device, or combinations thereof. For example, the medical device 102 may comprise a medical therapy delivery device, a medical device configured to sense a parameter of the subject, a medical device configured to diagnose a condition, a medical device configured to sample one or more tissues and/or fluids from a subject, or combinations thereof.

The medical device 102 may be utilized alone to provide a medical service (e.g., diagnostic, monitoring, therapeutic, or combinations thereof) to a subject or may be utilized with one or more medical devices 103 (e.g., a medical device internal or external to the subject that is electrically and/or mechanically coupled to the medical device 102). For example, the medical device 102 and/or device 103 may comprise devices such as a pacemaker, defibrillator, monitoring device, infusion device, neurostimulator, gastric stimulator, cochlear device, or any other device that is at least partially subcutaneously implanted in a subject.

In some embodiments, at least a portion of the medical device 102 is positioned proximate the nervous system of a subject (e.g., proximate the spinal cord or canal, brain, and/or peripheral nervous system). The medical device 102 may be a catheter, a lead, or lead extension. For example, the medical device 102 may be a lead including one or more electrodes on a distal end portion of the lead. Electrical contacts in the lead may be electrically coupled (e.g., physically or wirelessly) to a control module having an electrical signal generator (e.g., medical device 103 external or internal to the subject) and signals generated by the medical device 103 may be delivered to the subject via the electrodes. In some embodiments, such leads are utilized as implantable stimulation devices, which may be utilized in a variety of treatments and procedures, such as, for example, spinal cord stimulation. For example, implantable stimulation devices may be used to stimulate nerves, such as the spinal cord, muscles, or other tissue. The stimulator electrodes of the leads may be implanted in contact with or near the nerves, muscles, or other tissue to be stimulated. A pulse generator of the medical device 103 generates electrical pulses that are delivered by the electrodes to body tissue. In such embodiments, the lead is anchored at one or more places in the subject to prevent or reduce movement of the lead or stimulator electrodes within the subject (e.g., during short-term or long-term placement of the devices 102, 103 in the subject) that could damage tissue, move the stimulator electrodes out of the desired position, or interrupt the connection between the stimulator electrodes and the medical device 102, 103.

As shown in FIG. 1, the anchor element 100 is placed over at least a portion of the medical device 102 (e.g., a cannula of the medical device 102). For example, at least a portion of the medical device 102 may be positioned within a lumen formed by the tubular body (e.g., cannula) of the anchor element 100. As depicted, the anchor element 100 is shown in a deployed state where one or more protrusions (e.g., one, two, three, four, or more lobes 104, e.g., circumferentially spaced lobes) extend outwardly from a portion of the anchor element 100 (e.g., laterally outward from a longitudinal axis or centerline of the anchor element 100). Each lobe 104 extending laterally from the anchor element 100 may form an opening 107 within the lobe 104.

When attached to the medical device 102, the lobes 104 of the anchor element 100 may anchor the medical device 102 by engaging with one or more portions of the subject. For example, the lobes 104 of the anchor element 100 may engage with a portion of the subject's tissue (e.g., muscle tissue, nervous tissue, connective tissue, etc.) to at least partially retain the medical device 102 in a desired position within the subject. It is also believed that, in some embodiments, regrowth of the tissue of the subject proximate the lobes 104 may intertwine with at least a portion of the lobes 104 (e.g., tissue may extend through the openings 107) further anchoring the anchor element 100 and medical device 102 within the subject.

The anchor element 100 may be coupled (e.g., mechanically coupled) to at least a portion of the medical device 102 (e.g., an outer portion or exterior surface of the medical device 102). For example, the anchor element 100 may be secured to the medical device 102 through mechanical interference (e.g., utilizing friction, compression, swaging, etc.) rather than through adhesion or the use of fasteners. The anchor element 100 may include one or more portions for retaining the anchor element 100 to the medical device 102. For example, engagement portions 106, 108 may be formed on either side of the lobes 104 and may act to secure the anchor element 100 to the medical device 102 (e.g., via a mechanical interference fit). In some embodiments, each of the engagement portions 106, 108 of the anchor element 100 include an inner dimension (e.g., diameter) that is smaller than an outer dimension (e.g., diameter) of the medical device 102. One or more portions of the anchor element 100 (e.g., engagement portions 106, 108) may be formed from a flexible material (e.g., an elastically deformable material) such as, for example, a polymer (e.g., silicone, polyurethane, etc.). The flexible engagement portions 106, 108 may be deformed (e.g., elastically deformed) to enlarge a cross-sectional area of a lumen formed within each of the engagement portions 106, 108. The enlarged engagement portions 106, 108 may be positioned over (e.g., around, about) the medical device 102. As the enlarged engagement portions 106, 108 are allowed to contract back to substantially their original size (e.g., cross-sectional area), the engagement portions 106, 108 may engage and couple with the medical device 102.

In some embodiments, one or more ends of the anchor element 100 include a taper 110 or chamfer to assist in insertion of the anchor element 100 into the subject.

Figure 2A:
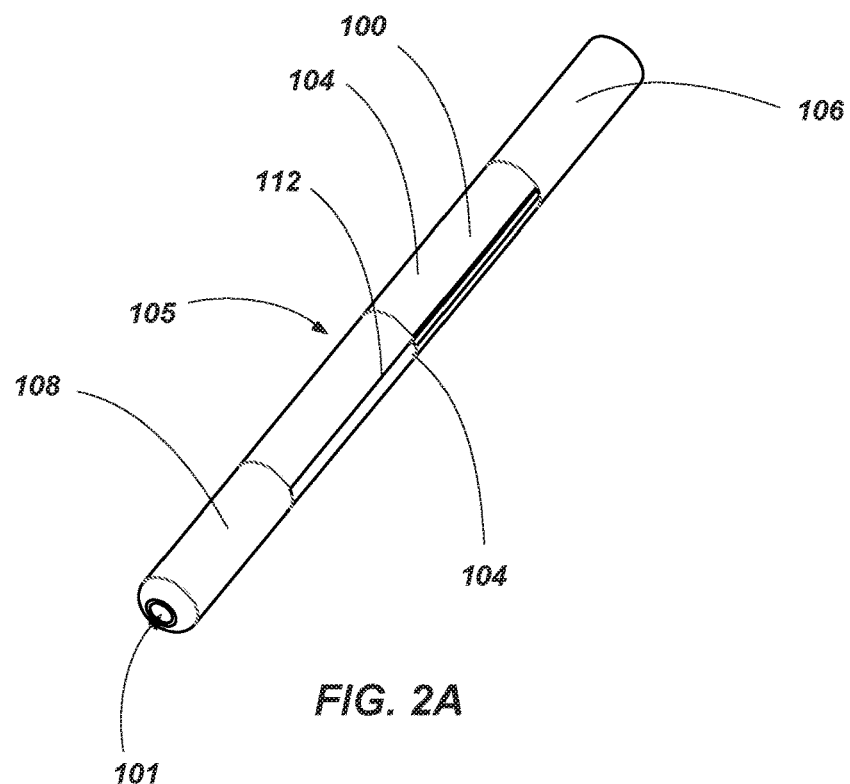
FIGS. 2A and 2B depict an anchor element in accordance with an embodiment hereof in an initial state and a deployed state, respectively.
Figure 2B:
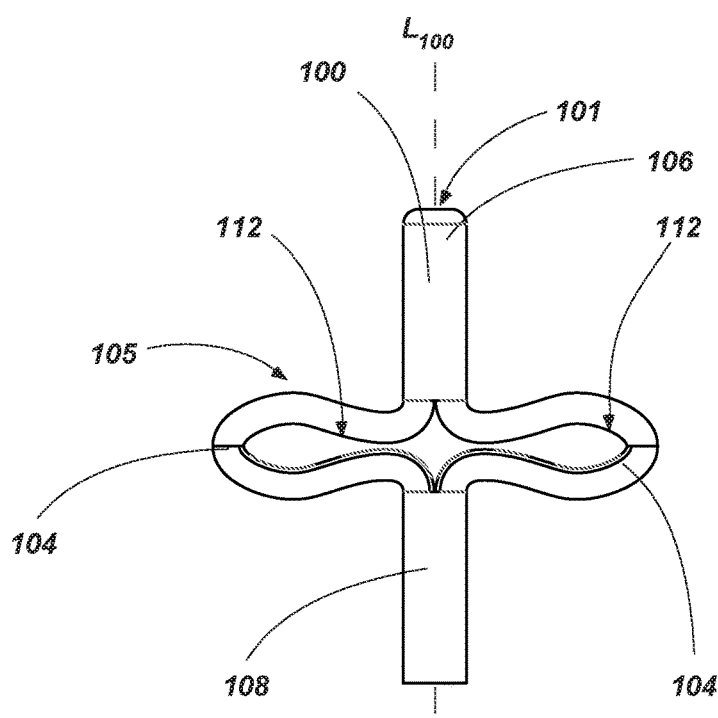

FIGS. 2A and 2B depict an anchor element (e.g., anchor element 100) in an initial state (e.g., a retracted or relaxed state) and a deployed state (e.g., a semi-distended state of the inner diameter), respectively. As shown in FIG. 2A, the anchor element 100 includes a protrusion or lobe portion 105 positioned between the engagement portions 106, 108 of the anchor element 100. The body of the anchor element 100 may form a lumen 101 therein. The lobes 104 (e.g., two lobes 104) of the lobe portion 105 are formed about the anchor element 100 (e.g., at equal circumferential spacing) by slits 112 in the tubular body of the anchor element 100. In the initial state, the lobe portion 105 of the anchor element 100 is substantially parallel to (e.g., coextensive with) a longitudinal axis L100 of the anchor element 100.

Referring also to FIG. 2B, the engagement portions 106, 108 may be moved toward each other to transition the anchor element 100 to the deployed state. The slits 112 enable the lobes 104 to extend outwardly (e.g., in a direction lateral or transverse (e.g., perpendicular) to the longitudinal axis L100 of the anchor element 100) from a portion of the anchor element 100 (e.g., from the engagement portions 106, 108).

Figure 3A:
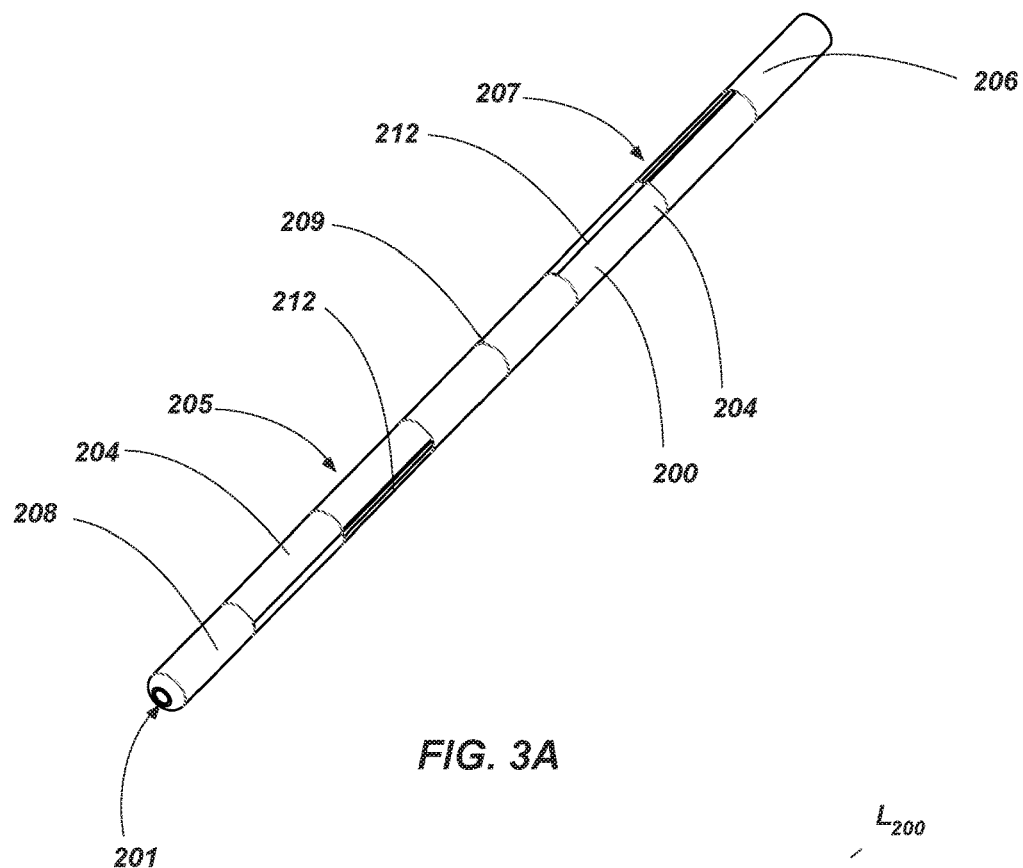
FIGS. 3A and 3B depict an anchor element in accordance with an embodiment hereof in an initial state and a deployed state, respectively.
Figure 3B:
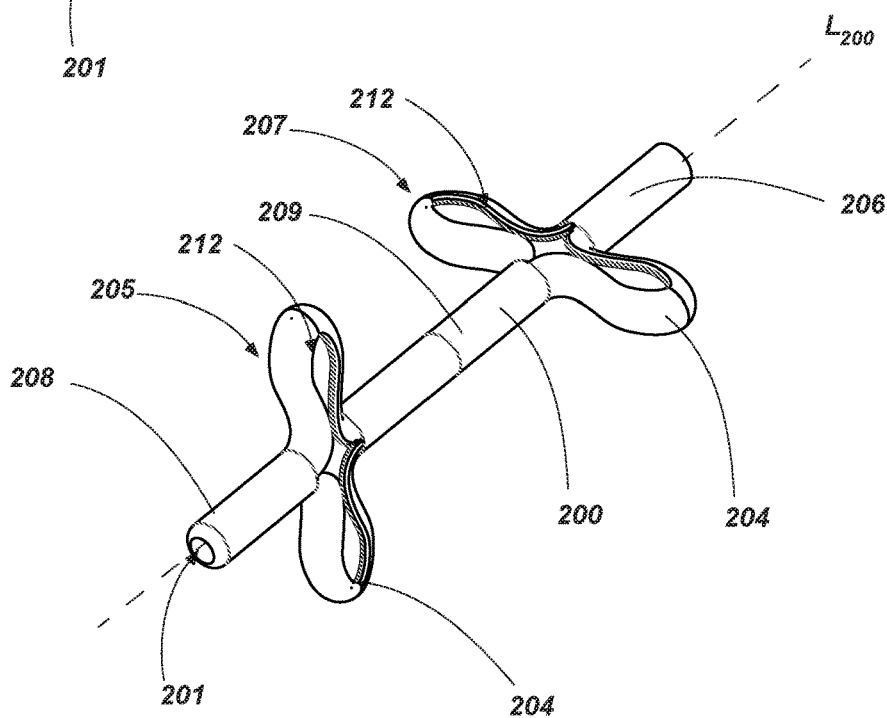

FIGS. 3A and 3B depict an anchor element 200 in an initial state (e.g., a retracted state) and a deployed state, respectively. As shown in FIG. 3A, the anchor element 200 may be somewhat similar to anchor element 100 discussed above and the body of the anchor element 200 may form a lumen 201 therein. However, anchor element 200 may include more than one lobe portion (e.g., two lobe portions 205, 207) positioned between the engagement portions 206, 208 of the anchor element 200. In other embodiments, the anchor element 200 includes three, four, or more lobe portions. Lobes 204 (e.g., two lobes) of each lobe portion 205, 207 are formed about the anchor element 200 (e.g., at equal circumferential spacing) by slits 212 in the tubular body of the anchor element 200. In the initial state, the lobe portions 205 of the anchor element 200 are substantially parallel to (e.g., coextensive with) a longitudinal axis L200 of the anchor element 200.

In some embodiments, the anchor element 200 includes an additional engagement portion 209 positioned between the lobe portions 205, 207.

Referring also to FIG. 3B, the engagement portions 206, 208 may be moved toward each other (e.g., toward the additional engagement portion 209) to transition the anchor element 200 to the deployed state. The slits 212 enable the lobes 204 to extend outwardly (e.g., in a direction lateral or transverse (e.g., perpendicular) to a longitudinal axis L200 of the anchor element 200) from a portion of the anchor element 200 (e.g., from the engagement portions 206, 208). As depicted, the lobe portions 205, 207 may be offset from one another (e.g., offset 90 degrees about the longitudinal axis L200 of the anchor element 200).

Figure 4:
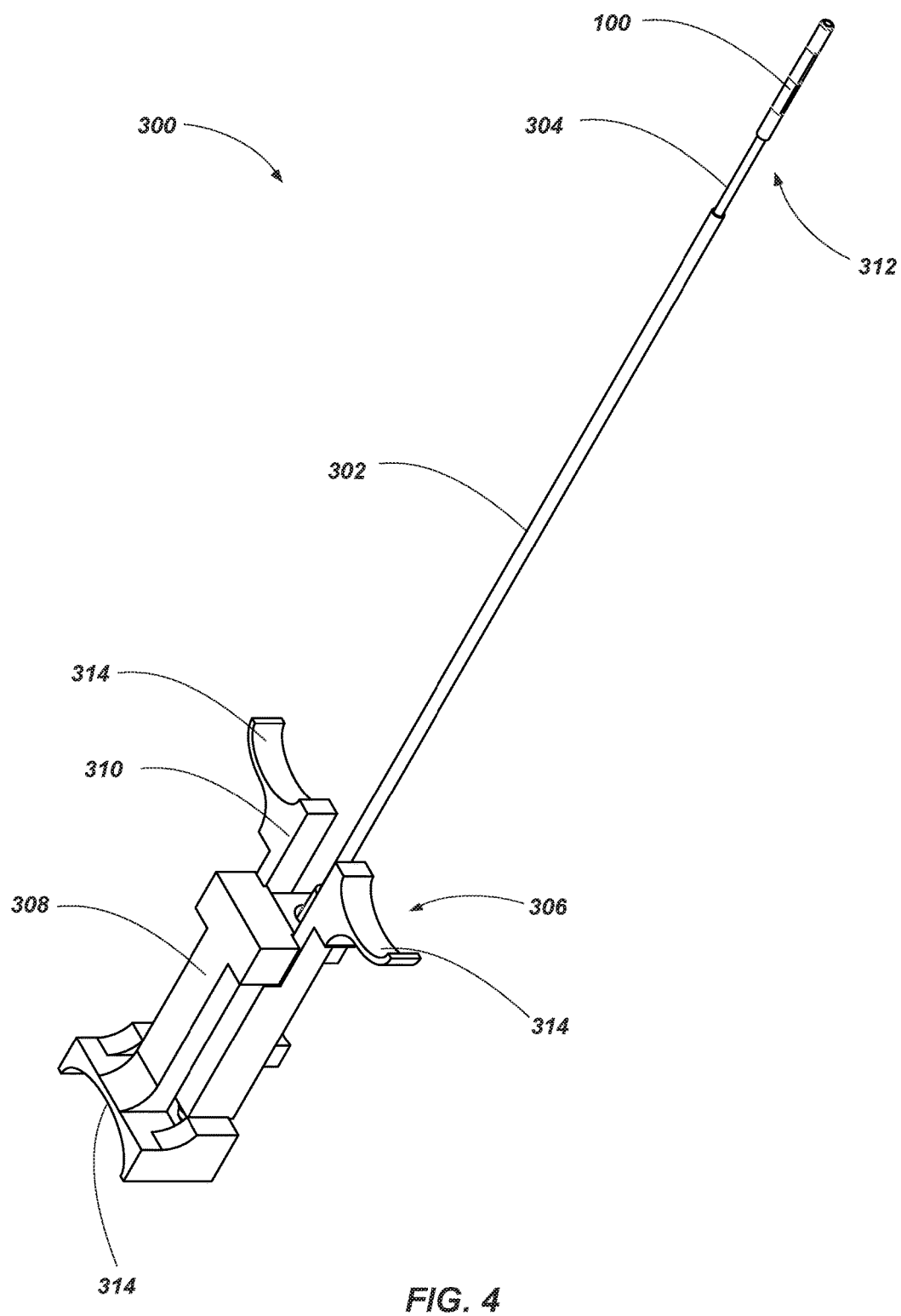
FIG. 4 depicts an anchor deployment device in accordance with one embodiment.

FIG. 4 depicts an anchor deployment device 300 that may be utilized with an anchor element (e.g., anchor elements 100, 200 discussed above with reference to FIGS. 1 through 3B). As shown in FIG. 4, the anchor deployment device 300 includes a first cannula (e.g., deployment cannula 302) and a second cannula (e.g., anchor cannula 304) received at least partially within the deployment cannula 302. For example, the deployment cannula 302 may have an inner dimension (e.g., diameter) that is greater than an outer dimension (e.g., diameter) of the anchor cannula 304 such that the anchor cannula 304 may be received and movable within the deployment cannula 302. The anchor deployment device 300 may include a handle 306 having a first portion 308 coupled to the deployment cannula 302 and a second portion 310 coupled to the anchor cannula 304. The portions 308, 310 of the handle 306 may be movable relative to one another (e.g., the second portion 310 may slide relative to the first portion 308) in order to move the anchor cannula 304 within the deployment cannula 302. Each portion 308, 310 of the handle 306 may include one or more grips 314 enabling a user (e.g., medical practitioner) to actuate the handle 306, thereby sliding the second portion 310 relative to the first portion 308 along a common axis.

As depicted, the anchor cannula 304 may be sized to receive an anchor element (e.g., anchor element 100) on the anchor cannula 304 at distal portion 312 of the anchor deployment device 300. The outer dimension (e.g., diameter) of the anchor cannula 304 may be greater than the inner dimension (e.g., diameter) of the anchor element 100. Such a diameter of the anchor cannula 304 may act to enlarge a cross-sectional area of a lumen 101 formed within a portion of the anchor element 100 (e.g., at each of the engagement portions 106, 108 (FIG. 1)) to form an initial dimension to an enlarged dimension. For example, the anchor cannula 304 may deform (e.g., elastically deform) the anchor element 100 to a dimension (e.g., diameter) that is greater than a dimension (e.g., diameter) of the medical device 102 (FIG. 1) on which the anchor element 100 is to be placed.

Figure 5:
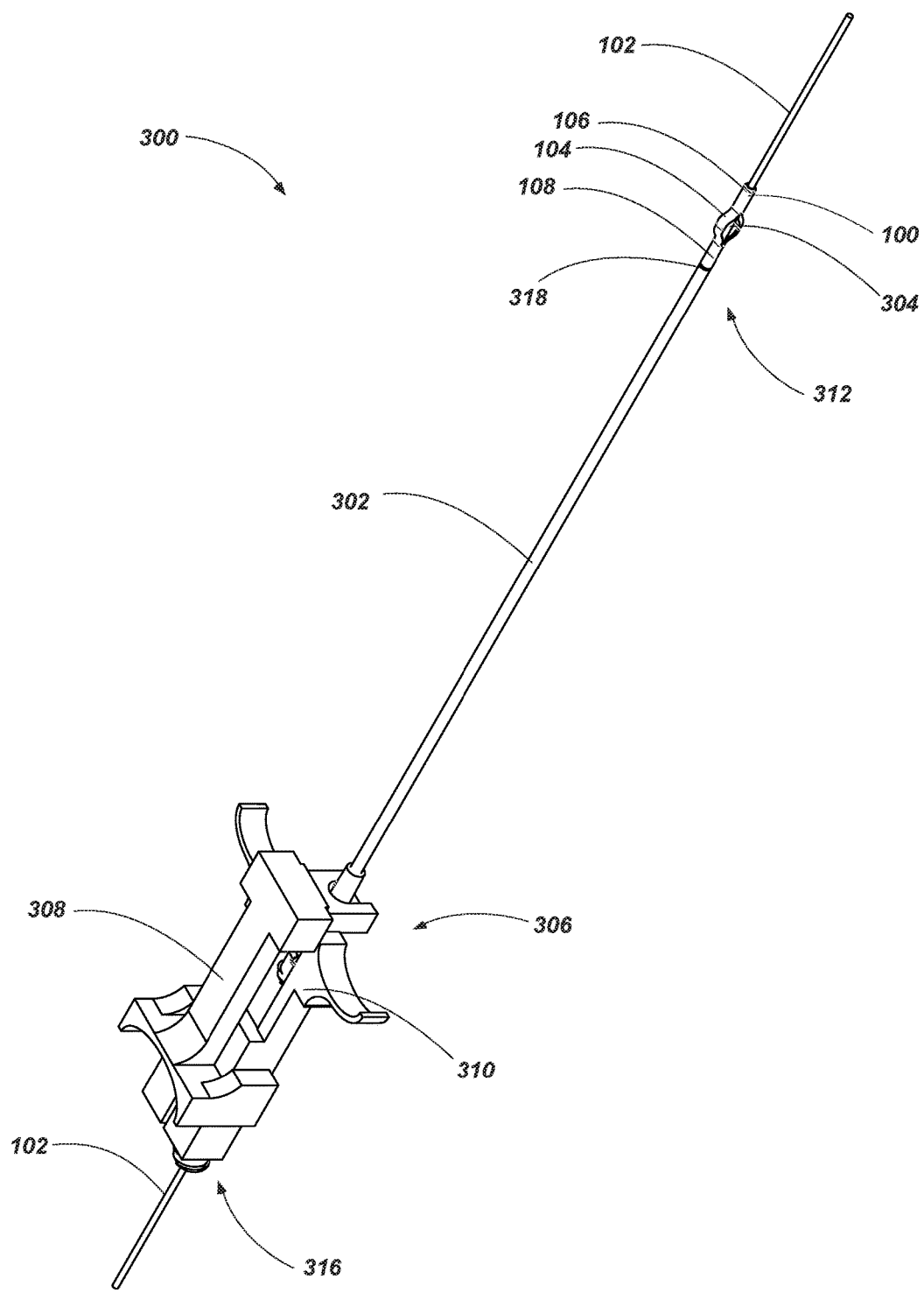
FIG. 5 depicts a view of the anchor deployment device shown in FIG. 4 beginning to deploy an anchor element.

FIG. 5 depicts a view of the anchor deployment device 300 shown in FIG. 4 beginning to deploy an anchor element (e.g., anchor element 100 in a distended state of the inner diameter). As shown in FIG. 5, at least a portion of a medical device (e.g., medical device 102) may be received within a portion of the anchor deployment device 300. For example, the anchor cannula 304 may have an inner dimension (e.g., diameter) that is sized to enable at least a portion of the medical device 102 to be received within the anchor cannula 304. In some embodiments, a proximal portion 316 of the anchor deployment device 300 is configured such that the medical device 102 extends through the anchor deployment device 300 and out of the of the anchor deployment device 300 at the proximal portion 316. Such a configuration may enable a user to position the anchor deployment device 300 along and through the medical device 102 in order to secure an anchor element 100 to the anchor deployment device 300 at any desired position. For example, the medical device 102 may be placed within a subject and the anchor deployment device 300 may be slid along the medical device 102. A portion of the anchor deployment device 300 (e.g., the distal portion 312) may be inserted within the subject to secure the anchor element 100 within the subject while the medical device 102 resides within the subject.

Actuation of the handle 306 may bring the anchor element 100, which is positioned on the anchor cannula 304 (e.g., in a radially enlarged or stretched state), into contact with the deployment cannula 302 (e.g., a leading end 318 of the deployment cannula 302). The deployment cannula 302 may act to force (e.g., slide) at least a portion of the anchor element 100 along the anchor cannula 304. For example, the deployment cannula 302 may force the first engagement portion 106 toward the second engagement portion 108, thereby deploying the lobes 104 of the anchor element 100. As the anchor cannula 304 is slid within the deployment cannula 302, the leading end 318 of the deployment cannula 302 may force the anchor element 100 off of the anchor cannula 304 and onto the medical device 102 (e.g., into the position shown in FIG. 1).

Figure 6:
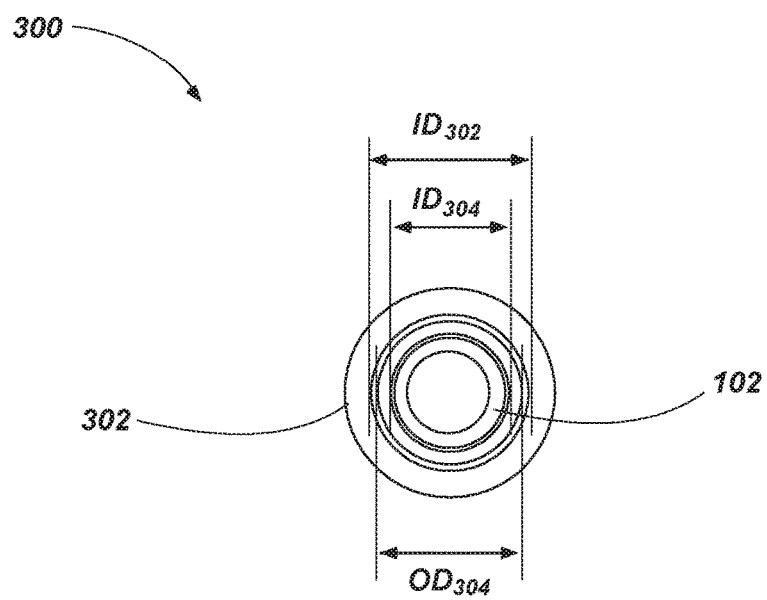
FIG. 6 depicts a cross-sectional view of a portion of the anchor deployment device shown in FIG. 4 with a medical device received in the anchor deployment device.

FIG. 6 depicts a cross-sectional view of a portion of the anchor deployment device 300 shown in FIG. 4 with the medical device 102 received in the anchor deployment device 300. As shown in FIG. 6, the inner diameter ID304 of the anchor cannula 304 is sized to enable the medical device 102 to be received within the anchor cannula 304. The inner diameter ID302 of the deployment cannula 302 may be greater than an outer dimension OD304 of the anchor cannula 304 such that the anchor cannula 304 may be received and movable within the deployment cannula 302.

Figure 7:
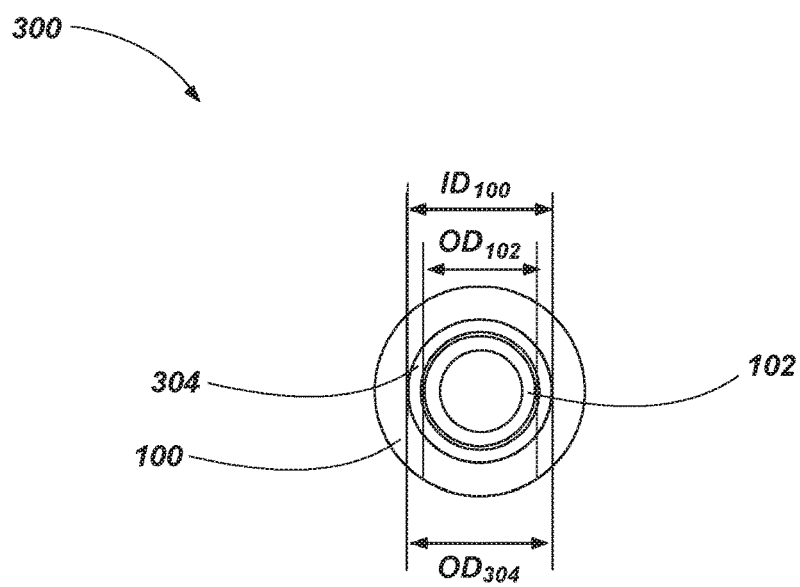
FIG. 7 depicts another cross-sectional view of a portion of the anchor deployment device shown in FIG. 4 with the medical device received in the anchor deployment device and an anchor element attached to the anchor deployment device.

FIG. 7 depicts another cross-sectional view of a portion of the anchor deployment device 300 shown in FIG. 4 with the medical device 102 received in the anchor deployment device 300 and the anchor element 100 attached to the anchor deployment device 300. The outer diameter OD304 of the anchor cannula 304 may be greater than an inner diameter of the anchor element 100 such that the anchor cannula 304 acts to enlarge a cross-sectional area of the lumen formed within a portion of the anchor element 100 to form an enlarged inner diameter ID100 of the anchor element 100 that is substantially equal to the outer diameter OD304 of the anchor cannula 304. The enlarged inner diameter ID100 of the anchor element 100 may be greater than an outer diameter OD102 of the medical device 102 such that the enlarged inner diameter ID100 of the anchor element 100 may be deployed over the outer diameter OD102 of the medical device 102. When the anchor element 100 is removed from the anchor cannula 304 (e.g., by the deployment cannula 302 as discussed above), the anchor element 100 may contract toward the initial diameter to the anchor element 100 (e.g., where the initial diameter of the anchor element 100 is less than the outer diameter OD102 of the medical device 102) in order to secure the anchor element 100 to the medical device 102.

Figure 8A:
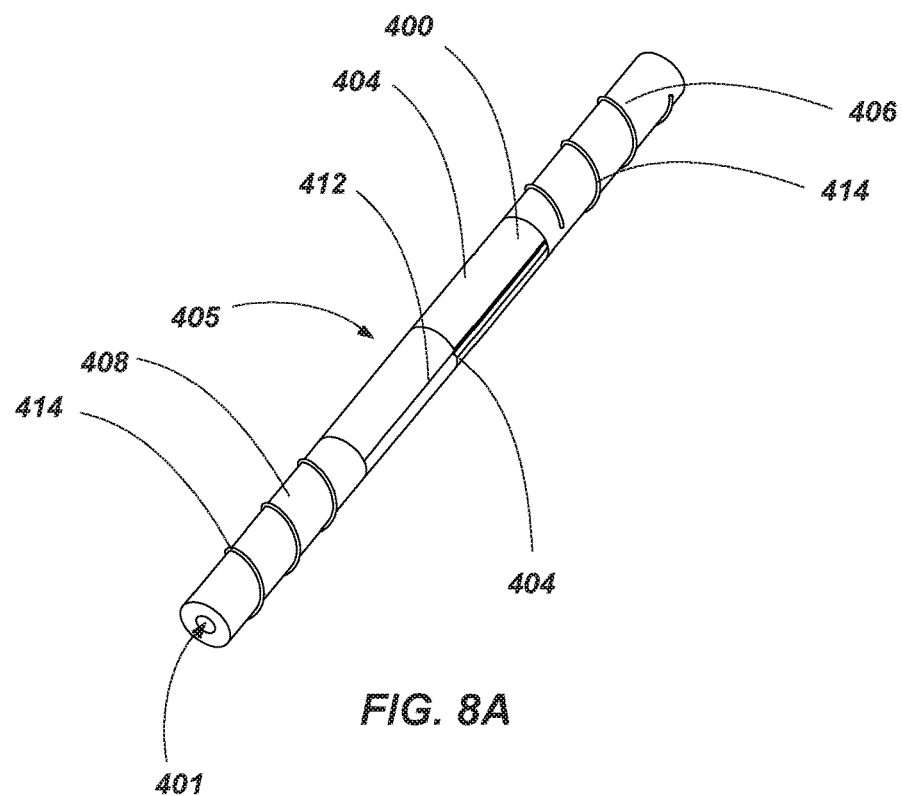
FIGS. 8A and 8B depict an anchor element in accordance with an embodiment hereof in an initial state and a deployed state, respectively.
Figure 8B:
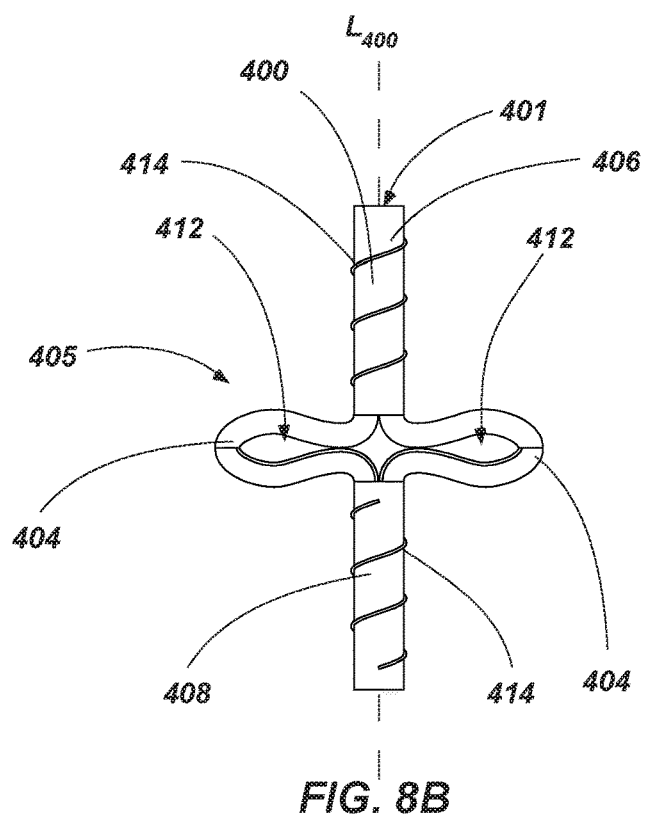

FIGS. 8A and 8B depict an anchor element 400 in an initial state and a deployed state, respectively. The anchor element 400 may be similar to and include one or more of the same features and functioning as the anchor elements 100, 200 discussed above with reference to FIGS. 1 through 3B. As shown in FIG. 8A, the anchor element 400 includes a lobe portion 405 positioned between the engagement portions 406, 408 of the anchor element 400. The body of the anchor element 400 may form a lumen 401 therein. Lobes 404 (e.g., two lobes) of the lobe portion 405 are formed about the anchor element 400 (e.g., at equal circumferential spacing) by slits 412 in the tubular body of the anchor element 400. In the initial state, the lobe portion 405 of the anchor element 400 is substantially parallel to (e.g., coextensive with) a longitudinal axis L400 of the anchor element 400.

Referring also to FIG. 8B, the engagement portions 406, 408 may be moved toward each other to transition the anchor element 400 to the deployed state. The slits 412 enable the lobes 404 to extend outwardly (e.g., in a direction lateral or transverse (e.g., perpendicular) to the longitudinal axis L400 of the anchor element 400) from a portion of the anchor element 400 (e.g., from the engagement portions 406, 408).

As depicted, the anchor element 400 may include a biasing feature (e.g., a radial biasing feature). For example, the anchor element 400 may include one or more springs 414 extending about at least a portion of the anchor element 400 (e.g., the engagement portions 406, 408). In some embodiments, the springs 414 are disposed on an exterior portion of the anchor element 400. In other embodiments, the springs 414 may be disposed within the anchor element 400. The springs 414 may act to bias the anchor element 400 in (e.g., toward) an initial state. For example, the springs 414 may act to radially bias the engagement portions 406, 408 of the anchor element 400 inward in a direction toward the lumen 401 (e.g., constricting the lumen 401) such that the springs 414 bias the engagement portions 406, 408 to or toward an initial state (e.g., an unstretched inner diameter of the anchor element 400). In some embodiments, the springs 414 act to relatively more rapidly tighten the anchor element 400 around a medical device 102 (see, e.g., FIG. 5).

It is noted that any anchor element disclosed herein (e.g., anchor elements 100, 200) may include a radial biasing feature (e.g., springs). In other embodiments, the anchor element may include an axial biasing feature.

Figure 9:
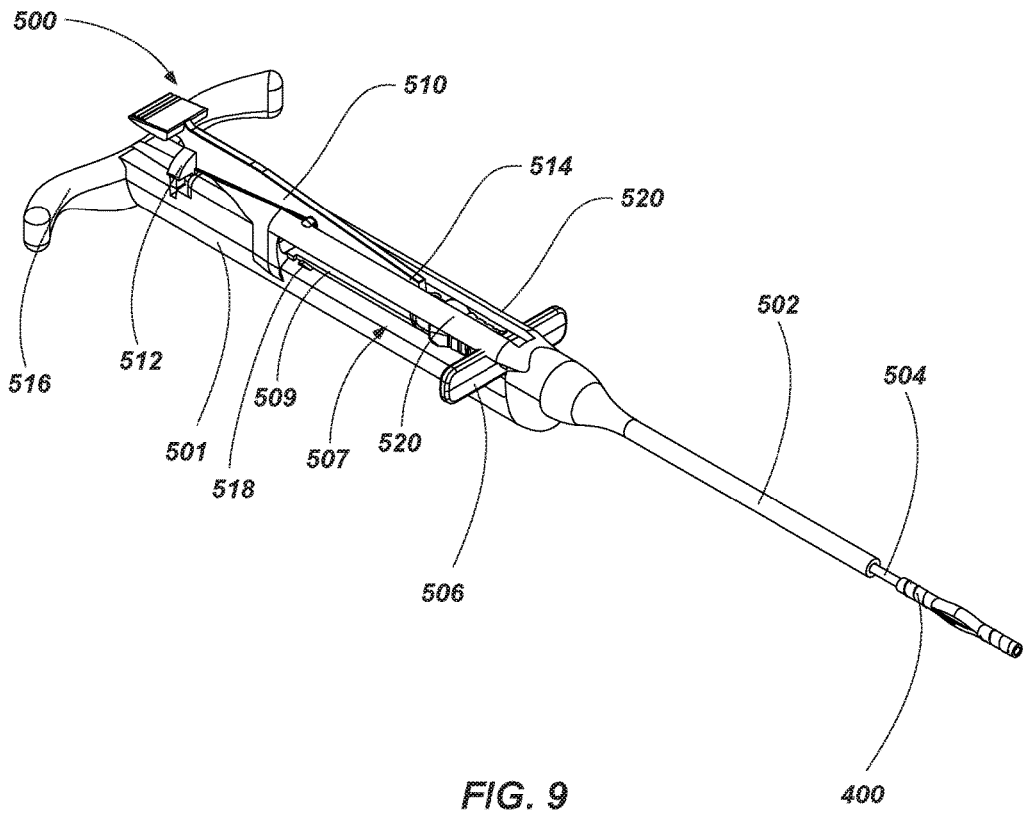
FIGS. 9 and 10 depict a perspective view and a side view, respectively, of an anchor deployment device in accordance with an embodiment of the disclosure.
Figure 10:
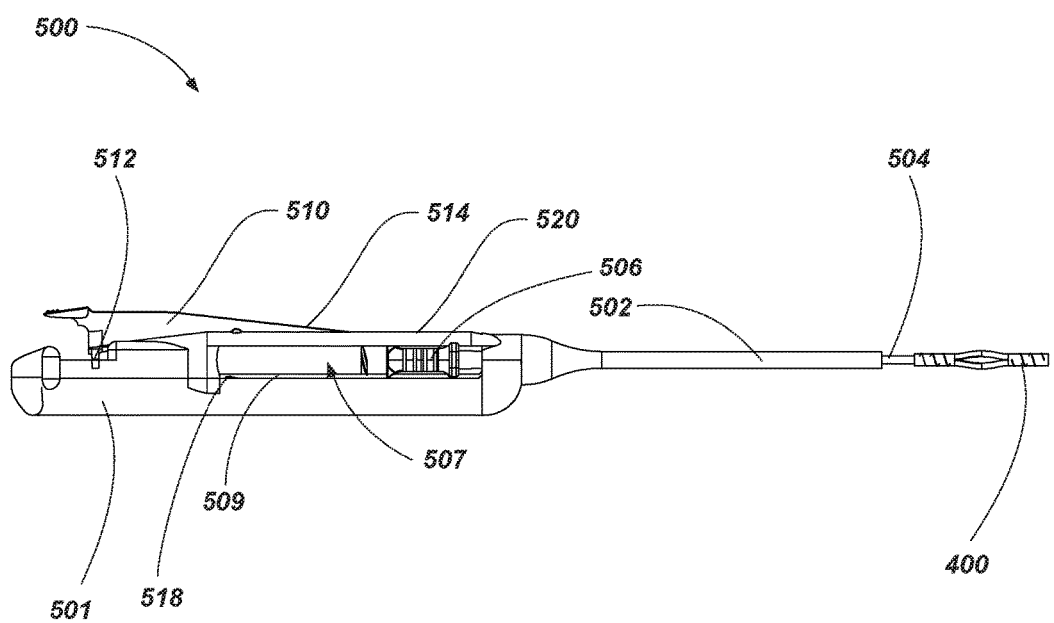

FIGS. 9 and 10 depict a perspective view and a side view, respectively, of an anchor deployment device 500. The anchor deployment device 500 may be similar to and include one or more of the same features and functioning as the anchor deployment device 300 discussed above with reference to FIGS. 4 through 7. As shown in FIGS. 9 and 10, the anchor deployment device 500 includes a first cannula (e.g., deployment cannula 502) and a second cannula (e.g., anchor cannula 504) received at least partially within the deployment cannula 502. The anchor deployment device 500 may include a handle 506 (e.g., formed as a hub) coupled to the anchor cannula 504 such that the handle 506 and the anchor cannula 504 may be moved relative to another portion of the anchor deployment device 500 (e.g., a body 501 of the anchor deployment device 500). For example, the body 501 of the anchor deployment device 500 may define an opening or chamber 507 in which the handle 506 is at least partially disposed. In some embodiments, the body 501 of the anchor deployment device 500 defines a track 509 in the chamber 507 upon which a portion of the handle 506 (e.g., a complementary portion) may move along (e.g., slide) to guide (e.g., and retain) the handle 506 and the anchor cannula 504 relative to the body 501 and the deployment cannula 502. In some embodiments, the body 501 of the anchor deployment device 500 includes one or more straps 520 to assist in containing the handle 506 in the chamber 507. Movement of the handle 506 relative to the body 501 enables a user (e.g., medical practitioner) to slide the anchor cannula 504 relative to the deployment cannula 502 along a common axis.

As depicted, the anchor deployment device 500 is shown with an anchor element (e.g., anchor element 400 in a distended state of the inner diameter) positioned on the anchor cannula 504 of the anchor deployment device 500. As above, the anchor deployment device 500 may have an inner dimension (e.g., diameter) that is sized to enable at least a portion of a medical device 102 (FIG. 5) to be received within the anchor cannula 504. As also described above, the handle 506, the anchor cannula 504, and the deployment cannula 502 may be utilized to deploy one or more anchor elements on a medical device (e.g., anchor elements 100, 200, 400 on medical device 102 as shown and described above).

As further depicted in FIGS. 9 and 10, the anchor deployment device 500 may include an upper handle 510. A first end of the upper handle 510 may include a locking mechanism 512 that holds (e.g., locks, clamps, etc.) the medical device 102 (FIG. 5). For example, the locking mechanism 512 may secure the medical device 102 when an anchor element is being deployed on the medical device 102 (e.g., when at least a portion of the medical device 102 is resident in a subject).

A second end of upper handle 510 may include a securing member (e.g., a protrusion or elongated member 514) that engages with the handle 506 to secure the handle 506 and the anchor cannula 504. For example, the elongated member 514 of the upper handle 510 may retain the handle 506 and the anchor cannula 504 and prevent the handle 506 and the anchor cannula 504 from sliding relative to the body 501 of anchor deployment device 500.

The upper handle 510 may coupled to the body 501 (e.g., at a single point, location, or area) such that the first end and the second end of the upper handle 510 move (e.g., pivot) relative to each other. For example, when the locking mechanism 512 is securing the medical device 102 (FIG. 5), the elongated member 514 is disengaged with the handle 506, thereby enabling the handle 506 and the anchor cannula 504 to move relative to the body 501. Similarly, when the elongated member 514 is engaged with the handle 506 and restricting the handle 506 and the anchor cannula 504 from moving relative to the body 501, the locking mechanism 512 is disengaged from the medical device 102, thereby enabling the anchor deployment device 500 to move (e.g., slide) along the medical device 102. Such a configuration may enable the anchor deployment device 500 to be secured to the medical device 102 while an anchor element is being deployed and, likewise, secure the anchor deployment device 500 from any unwanted movement of the anchor cannula 504 relative to the deployment cannula 502 when the anchor deployment device 500 is being moved and positioned along the medical device 102.

The anchor deployment device 500 may include rear handle 516 that enables a user to move and position the anchor deployment device 500 along the medical device 102.

In some embodiments, the anchor deployment device 500 may include one or more ramps 518 positioned along the track 509 that may assist in retaining the handle 506 in a retracted position by engaging with a portion of the handle 506.

It is noted that to the extent that the anchor deployment devices are described in use with a particular anchor element, in other embodiments, the anchor deployment devices may be utilized with any suitable anchor element (e.g., anchor elements 100, 200, 400).

It is further noted that while the anchor elements and components of the anchor deployment device are primarily discussed herein as having a diameter, these elements are not necessarily limited to circular cross sections. For example, the anchor elements and components of the anchor deployment device, and the lumens formed therein, may have a square, circular, oval, rectangular, or any other suitable cross sectional shape.

Figure 11:
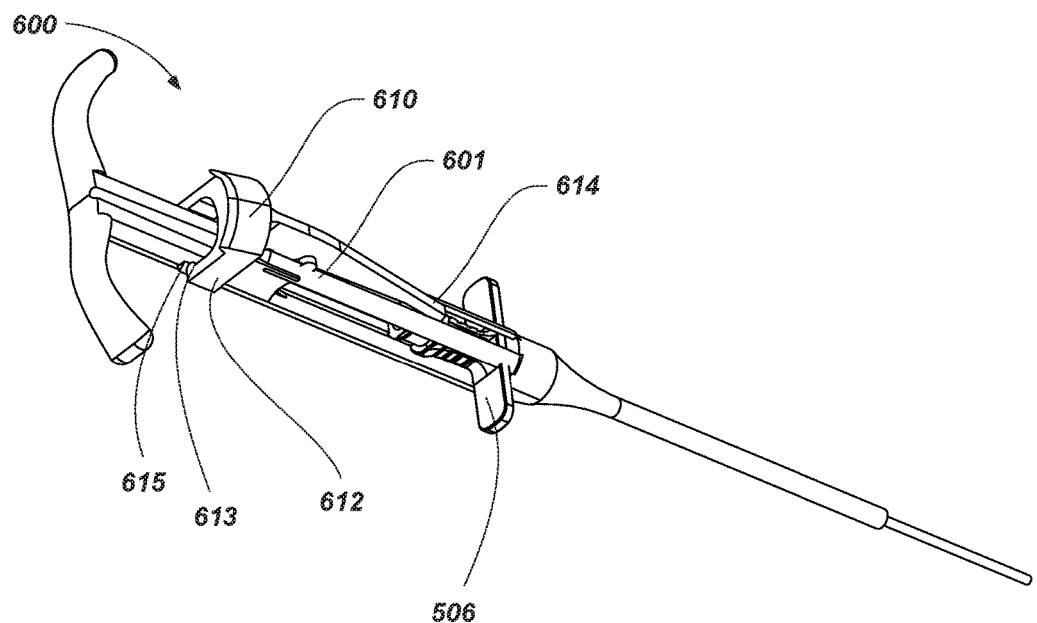
FIGS. 11 and 12 depict a perspective view and a cross-sectional side view, respectively, of an anchor deployment device in accordance with an embodiment of the disclosure.
Figure 12:
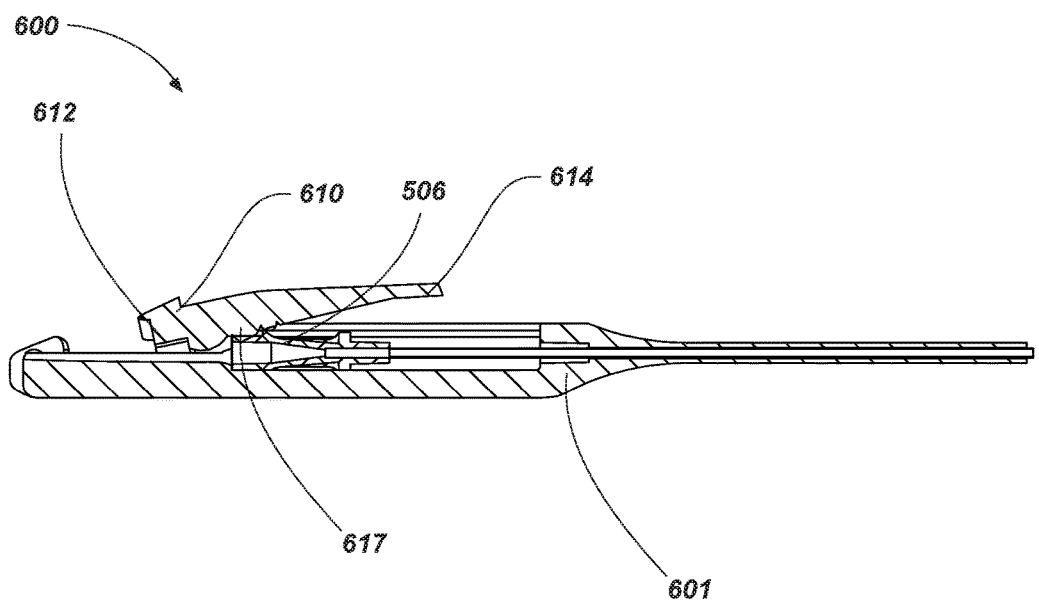

FIGS. 11 and 12 depict a perspective view and a cross-sectional side view, respectively, of an anchor deployment device 600. The anchor deployment device 600 may be substantially similar to the anchor deployment device 500 discussed above with reference to FIGS. 9 and 10. As shown in FIGS. 11 and 12, the anchor deployment device 600 may include upper handle 610, which may be substantially similar to upper handle 510 shown in FIGS. 9 and 10. A first end of upper handle 610 may substantially exhibit a U-shape or horseshoe shape including a locking mechanism 612 that holds (e.g., locks, clamps, etc.) the medical device 102 (FIG. 5). In order to lock or retain the upper handle 610 in a position holding the medical device 102, the locking mechanism 612 may include a protrusion 613 that is complementary to a protrusion 615 on the anchor deployment device 600 where interference between the protrusions 613, 615 will retain the locking mechanism 612 in the holding position (e.g., as depicted in FIG. 11).

In some embodiments, the upper handle 610 is sized such that movement of the handle 506 from a proximal position (e.g., as depicted in FIG. 11) toward a distal position (e.g., as depicted in FIG. 12) acts to release the locking mechanism 612 of the upper handle 610. For example, a middle, lower portion 617 of the upper handle 610 is positioned within a pathway of the handle 506 such that, when the handle 506 is moved from the proximal position toward the distal position, a portion of the handle 506 will contact the middle, lower portion 617 of the upper handle 610. Contact between the handle 506 and the middle, lower portion 617 of the upper handle 610 may act to force the upper handle 610 upwards, thereby, releasing the locking mechanism 612 of the upper handle 610.

As depicted, when the locking mechanism 612 of the upper handle 610 is engaged, an elongated member 614, which may be utilized to retain the handle 506 in the proximal position as depicted in FIG. 11, may be positioned entirely clear of a pathway of the handle, enabling the handle 506 to move relative to a body 601 of the anchor deployment device 600.

Figure 13:
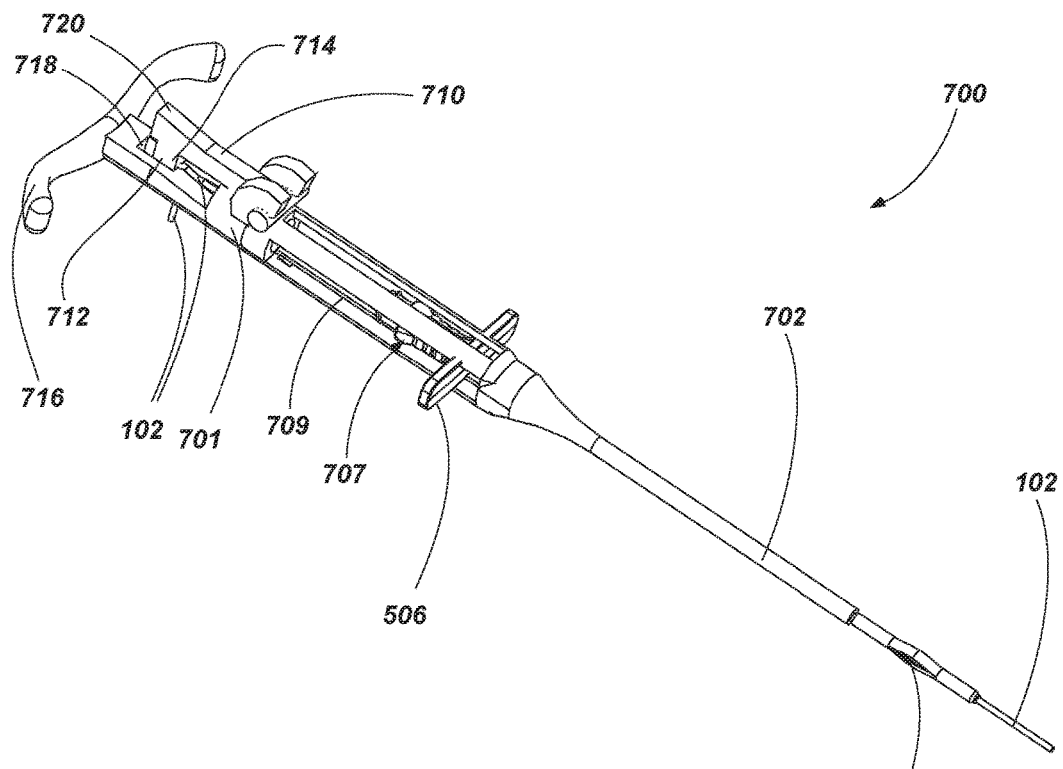
FIGS. 13 and 14 depict a perspective view and a cross-sectional side view, respectively, of an anchor deployment device in accordance with an embodiment of the disclosure.
Figure 14:
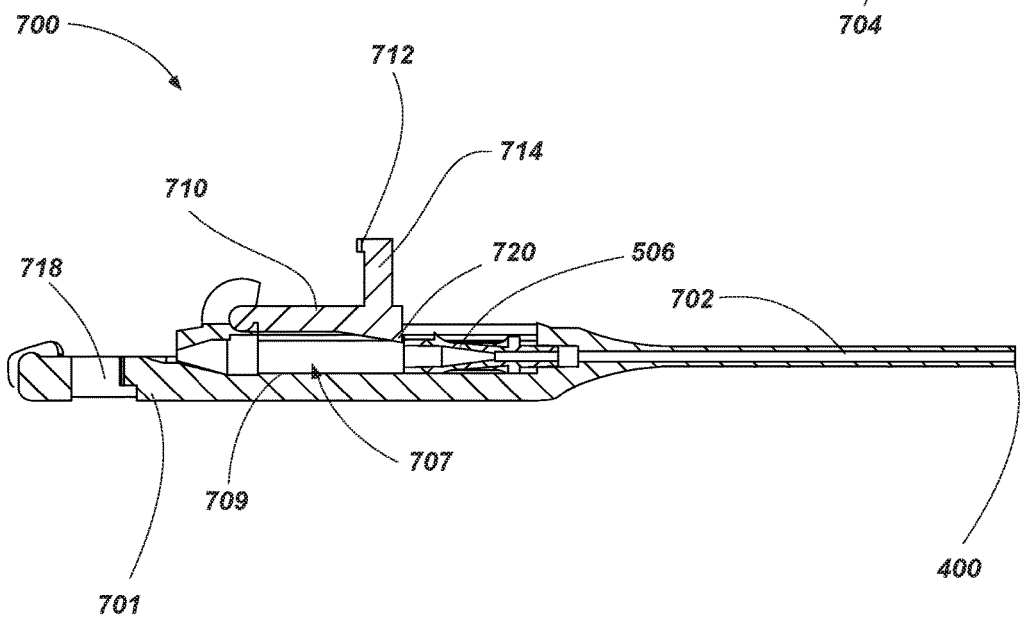

FIGS. 13 and 14 depict a perspective view and a cross-sectional side view, respectively, of an anchor deployment device 700. The anchor deployment device 700 may be similar to and include one or more of the same features and functioning as the anchor deployment devices 300, 500, 600 discussed above with reference to FIGS. 4 through 7 and 9 through 12. As shown in FIGS. 13 and 14, the anchor deployment device 700 includes a first cannula (e.g., deployment cannula 702) and a second cannula (e.g., anchor cannula 704) received at least partially within the deployment cannula 702. The anchor deployment device 700 may include the handle 506 coupled to the anchor cannula 704 such that the handle 506 and the anchor cannula 704 may be moved relative to another portion of the anchor deployment device 700 (e.g., a body 701 of the anchor deployment device 700). For example, the body 701 of the anchor deployment device 700 may define an opening or chamber 707 in which the handle 506 is at least partially disposed. In some embodiments, the body 701 of the anchor deployment device 700 defines a track 709 in the chamber 707 upon which a portion of the handle 506 (e.g., a complementary portion) may move along (e.g., slide) to guide (e.g., and retain) the handle 506 and the anchor cannula 704 relative to the body 701 and the deployment cannula 702. Movement of the handle 506 relative to the body 701 enables a user (e.g., medical practitioner) to slide the anchor cannula 704 relative to the deployment cannula 702 along a common axis.

The anchor deployment device 700 may include upper handle 710. For example, the upper handle 710 may be formed as a swingable or pivotable handle having a pivot point and an arm extending therefrom that moves between a medical device (e.g., a lead, a cannula, etc.) locking position (e.g., as depicted in FIG. 13) and a handle locking position (e.g., as depicted in FIG. 14). A first end of upper handle 710 (e.g., formed as a protrusion or elongated member 714) may include a locking mechanism 712 that holds (e.g., locks, clamps, engages, etc.) the medical device 102 in the medical device locking position. For example, the locking mechanism 712 may be received in an aperture 718 formed in the body 701 (e.g., and engage with a complementary portion of the body 701 within the aperture 718) to secure the medical device 102 (e.g., by clamping or otherwise trapping a portion of the medical device 102 against or relative to the body 701) when an anchor element is being deployed on the medical device 102 (e.g., when at least a portion of the medical device 102 is resident in a subject).

As depicted, a distal portion of the medical device 102 may extend through the aperture 718 in the body 701. For example, the distal portion of the medical device 102 may be turned (e.g., about 90 degrees) to extend downward through the aperture 718 to a position exterior to the body 701 of the anchor deployment device 700.

In the handle locking position, the same first end of the upper handle 710 (e.g., protrusion or ramp 720 formed on an opposing side of the upper handle 710 at the first end) engages with the handle 506 to secure the handle 506 and the anchor cannula 704. For example, the protrusion 720 of the upper handle 710 may retain the handle 506 and the anchor cannula 704 and prevent the handle 506 and the anchor cannula 704 from sliding relative to the body 701 of anchor deployment device 700.

As discussed above, the upper handle 710 may move (e.g., swing or pivot) to selectively position the locking mechanism 712 and the protrusion 720 proximate the handle 506 or the medical device 102. For example, when the locking mechanism 712 is securing the medical device 102 (FIG. 5), the protrusion 720 is disengaged with the handle 506, thereby enabling the handle 506 and the anchor cannula 704 to move relative to the body 701. Similarly, when the protrusion 720 is engaged with the handle 506 and restricting the handle 506 and the anchor cannula 704 from moving relative to the body 701, the locking mechanism 712 is disengaged from the medical device 102, thereby enabling the anchor deployment device 700 to move (e.g., slide) along the medical device 102. Such a configuration may enable the anchor deployment device 700 to be secured to the medical device 102 while an anchor element is being deployed and, likewise, secure the anchor deployment device 700 from any unwanted movement of the anchor cannula 704 relative to the deployment cannula 702 when the anchor deployment device 700 is being moved and positioned along the medical device 102.

The anchor deployment device 700 may include rear handle 716 that enables a user to move and position the anchor deployment device 700 along the medical device 102.

Figure 15:
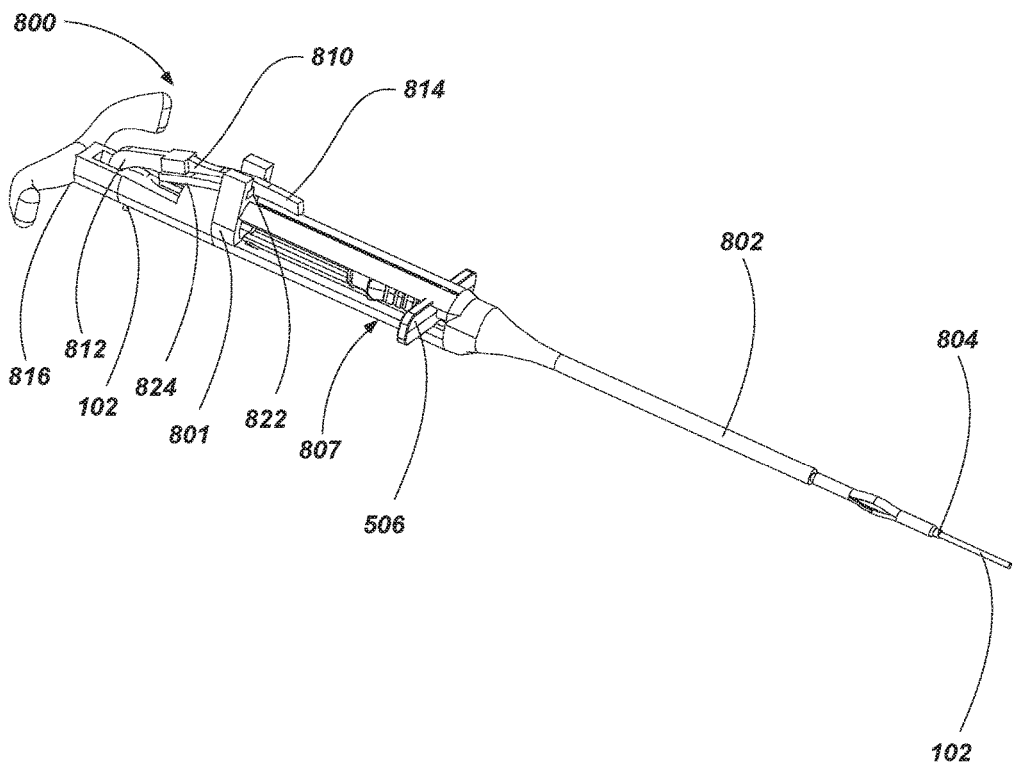
FIGS. 15 and 16 depict a perspective view and a cross-sectional side view, respectively, of an anchor deployment device in accordance with an embodiment of the disclosure.
Figure 16:
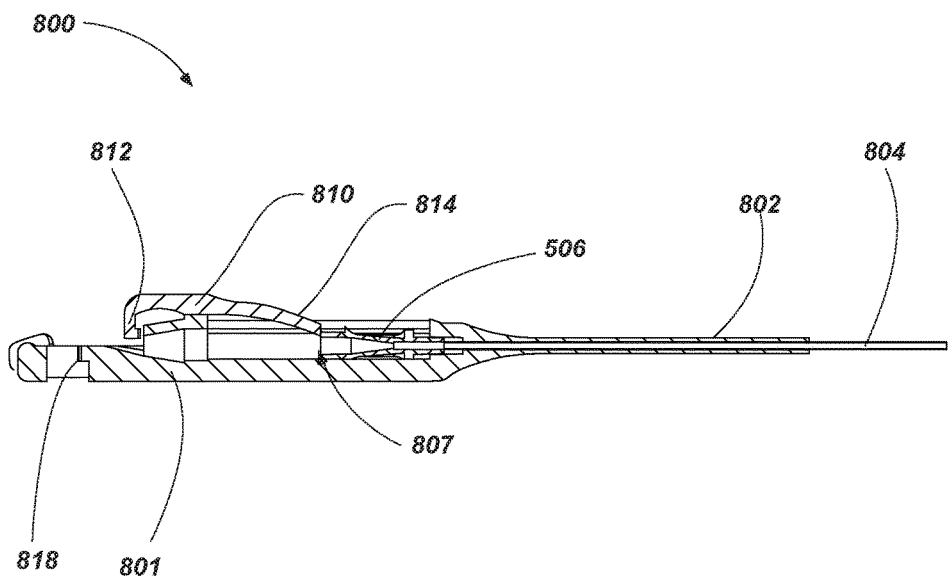

FIGS. 15 and 16 depict a perspective view and a cross-sectional side view, respectively, of an anchor deployment device 800. The anchor deployment device 800 may be similar to and include one or more of the same features and functioning as the anchor deployment devices 300, 500, 600, 700 discussed above with reference to FIGS. 4 through 7 and 9 through 14. As shown in FIGS. 15 and 16, the anchor deployment device 800 includes a first cannula (e.g., deployment cannula 802) and a second cannula (e.g., anchor cannula 804) received at least partially within the deployment cannula 802. The anchor deployment device 800 may include the handle 506 (e.g., formed as a hub) coupled to the anchor cannula 804 such that the handle 506 and the anchor cannula 804 may be moved relative to another portion of the anchor deployment device 800 (e.g., a body 801 of the anchor deployment device 800). For example, the body 801 of the anchor deployment device 800 may define an opening or chamber 807 in which the handle 506 is at least partially disposed. Movement of the handle 506 relative to the body 801 enables a user (e.g., medical practitioner) to slide the anchor cannula 804 relative to the deployment cannula 802 along a common axis.

The anchor deployment device 800 includes upper handle 810. For example, the upper handle 810 may be formed as a slidable handle that slides within a complementary groove 822 defined by the body 801 and moves between a medical device locking position (e.g., as depicted in FIG. 15) and a handle locking position (e.g., as depicted in FIG. 16). As depicted, the upper handle 810 may include a rail portion 824 that is received in the groove 822 to slidably couple the upper handle 810 to the body 801. A first end of upper handle 810 may include a locking mechanism 812 that holds (e.g., locks, clamps, etc.) the medical device 102. For example, the locking mechanism 812 may be received in an aperture 818 formed in the body 801 (e.g., and engage with a complementary portion of the body 801 within the aperture 818) to secure the medical device 102 (e.g., by clamping or otherwise trapping a portion of the medical device 102 against or relative to the body 801) when an anchor element is being deployed on the medical device 102 (e.g., when at least a portion of the medical device 102 is resident in a subject).

As depicted, a distal portion of the medical device 102 may extend through the aperture 818 in the body 801. For example, the distal portion of the medical device 102 may be turned (e.g., about 90 degrees) to extend downward through the aperture 818 to a position exterior to the body 801 of the anchor deployment device 800.

In the handle locking position, a second end of upper handle 810 may include a protrusion or elongated member 814 that engages with the handle 506 to secure the handle 506 and the anchor cannula 804. For example, the elongated member 814 of the upper handle 810 may retain the handle 506 and the anchor cannula 804 and prevent the handle 506 and the anchor cannula 804 from sliding relative to the body 801 of anchor deployment device 800.

The first end and the second end of the upper handle 810 move (e.g., slide) relative to the body 801 in order to move between the medical device locking position and the handle locking position. For example, when the locking mechanism 812 is securing the medical device 102, the elongated member 814 is disengaged with the handle 506, thereby enabling the handle 506 and the anchor cannula 804 to move relative to the body 801. Similarly, when the elongated member 814 is engaged with the handle 506 and restricting the handle 506 and the anchor cannula 804 from moving relative to the body 801, the locking mechanism 812 is disengaged from the medical device 102, thereby enabling the anchor deployment device 800 to move (e.g., slide) along the medical device 102. Such a configuration may enable the anchor deployment device 800 to be secured to the medical device 102 while an anchor element is being deployed and, likewise, secure the anchor deployment device 800 from any unwanted movement of the anchor cannula 804 relative to the deployment cannula 802 when the anchor deployment device 800 is being moved and positioned along the medical device 102.

The anchor deployment device 800 may include rear handle 816 that enables a user to move and position the anchor deployment device 800 along the medical device 102.

Figure 17:
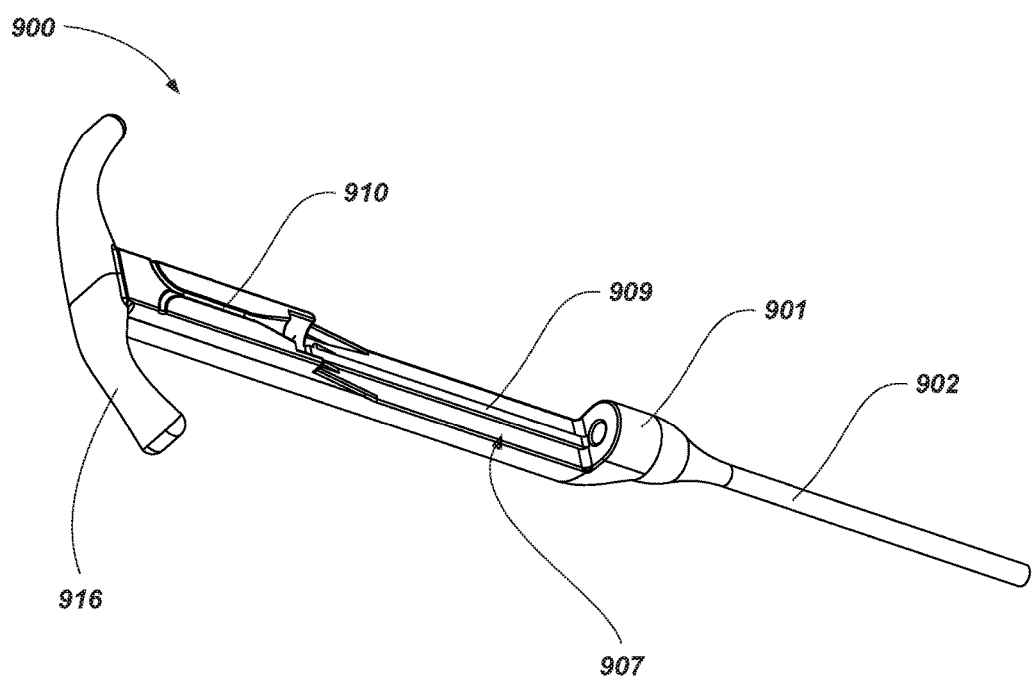
FIG. 17 depicts a perspective view of an anchor deployment device in accordance with an embodiment of the disclosure.

FIG. 17 depicts a perspective view of an anchor deployment device 900. The anchor deployment device 900 may be similar to and include one or more of the same features and functioning as the anchor deployment devices 300, 500, 600, 700, 800 discussed above with reference to FIGS. 4 through 7 and 9 through 16. As shown in FIG. 17, the anchor deployment device 900 includes a first cannula (e.g., deployment cannula 902) and a second or anchor cannula (not shown) received at least partially within the deployment cannula 902. The anchor deployment device 900 may include the handle 506 (see, e.g., FIGS. 9 and 10) coupled to the anchor cannula such that the handle 506 and the anchor cannula may be moved relative to another portion of the anchor deployment device 900 (e.g., a body 901 of the anchor deployment device 900). For example, the body 901 of the anchor deployment device 900 may define an opening or open recessed area 907 in which the handle 506 is at least partially disposed. As previously described, movement of the handle 506 relative to the body 901 enables a user (e.g., medical practitioner) to slide the anchor cannula relative to the deployment cannula 902 along a common axis (e.g., along track 909).

Unlike some of the other embodiments of anchor deployment devices disclosed herein, the anchor deployment device 900 may not include an additional handle for securing one or more of the handle 506 (see, e.g., FIGS. 9 and 10) and/or a portion of a medical device 102 (e.g., medical device 102 (FIG. 1)). Rather, the open recessed area 907 may enable a user open access to the handle 506 in order to move the handle 506 along the track 909 and secure the handle 506 in a position manually (e.g., by the user), for example, in a manner as discussed above when the anchor deployment device 900 is being moved and positioned along the medical device 102.

In some embodiments, the body 901 includes one or more recesses 910 (e.g., grooves or channels) to receive a portion of a portion of the medical device 102 (FIG. 1). As depicted, the recess 910 may extend along the body 901 and may extend laterally to a location exterior to the body 901 in one or more directions to enable a user to manually secure the medical device 102 (e.g., by the user's hand, finger(s), and/or thumb), for example, in a manner as discussed above when an anchor element is placed on the medical device 102.

The anchor deployment device 900 may include rear handle 916 that enables a user to move and position the anchor deployment device 900 along the medical device 102.

Figure 18:
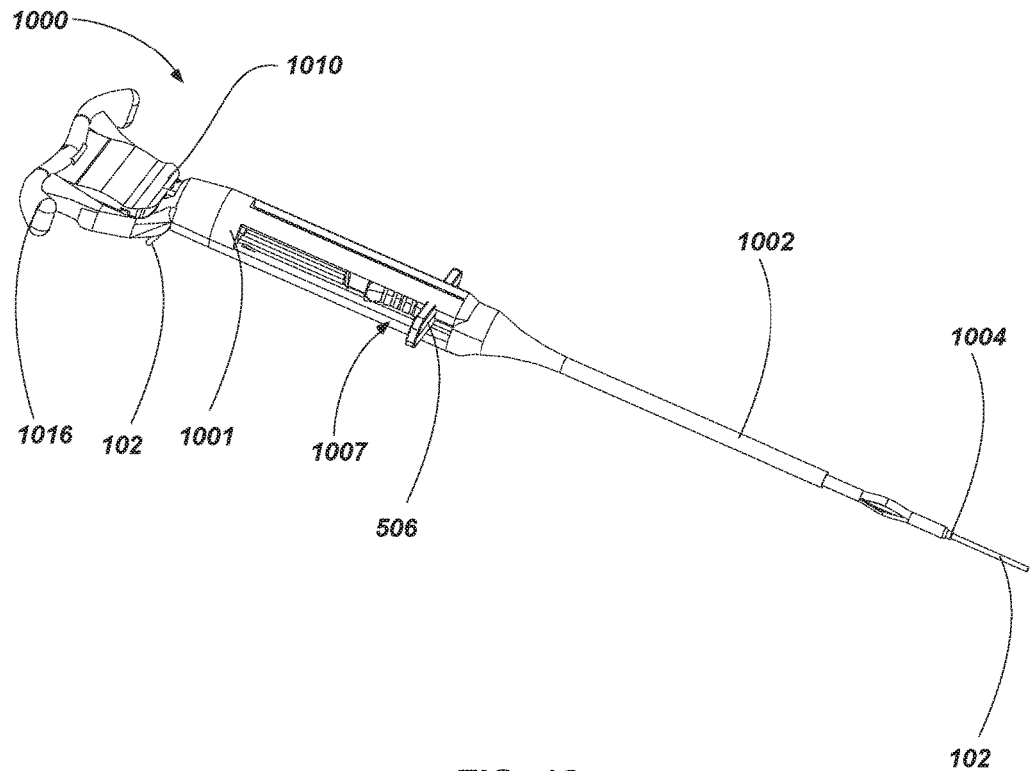
FIGS. 18 and 19 depict a perspective view and a side view, respectively, of an anchor deployment device in accordance with an embodiment of the disclosure.
Figure 19:
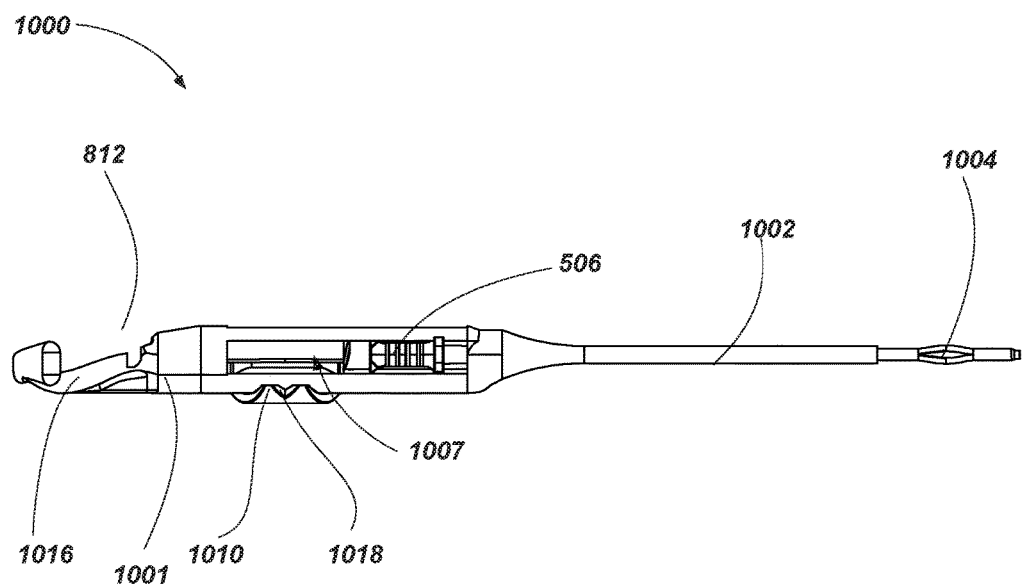

FIGS. 18 and 19 depict a perspective view and a cross-sectional side view, respectively, of an anchor deployment device 1000. The anchor deployment device 1000 may be similar to and include one or more of the same features and functioning as the anchor deployment devices 300, 500, 600, 700, 800, 900 discussed above with reference to FIGS. 4 through 7 and 9 through 17. As shown in FIGS. 18 and 19, the anchor deployment device 1000 includes a first cannula (e.g., deployment cannula 1002) and a second cannula (e.g., anchor cannula 1004) received at least partially within the deployment cannula 1002. The anchor deployment device 1000 may include the handle 506 (e.g., formed as a hub) coupled to the anchor cannula 1004 such that the handle 506 and the anchor cannula 1004 may be moved relative to another portion of the anchor deployment device 1000 (e.g., a body 1001 of the anchor deployment device 1000). For example, the body 1001 of the anchor deployment device 1000 may define an opening or chamber 1007 in which the handle 506 is at least partially disposed. Movement of the handle 506 relative to the body 1001 enables a user (e.g., medical practitioner) to slide the anchor cannula 1004 relative to the deployment cannula 1002 along a common axis.

The anchor deployment device 1000 includes at least one clip (e.g., clip 1010). For example, the clip 1010 may be configured to be positioned between a medical device locking position (e.g., as depicted in FIG. 18) and a handle locking position (e.g., as depicted in FIG. 19). In the medical device locking position, the clip 1010 may interface with a complementary portion of the body 1001 to hold (e.g., lock, clamp, etc.) the medical device 102. For example, clip 1010 may be received proximate (e.g., at) a rear handle 1016 of the body 1001, which enables a user to move and position the anchor deployment device 1000 along the medical device 102. The clip 1010 may engage with the body 1001 to secure the medical device 102 (e.g., by clamping or otherwise trapping a portion of the medical device 102 against or relative to the body 1001) when an anchor element is being deployed on the medical device 102 (e.g., when at least a portion of the medical device 102 is resident in a subject).

As depicted, a distal portion of the medical device 102 may extend downward through the body 1001 proximate the clip 1010. For example, the distal portion of the medical device 102 may be turned (e.g., about 90 degrees) to extend downward to a position exterior to the body 1001 of the anchor deployment device 1000. As best shown in FIG. 19, the clip 1010 may include an opening 1018 sized to enable the medical device 102 to pass through the clip 1010.

In the handle locking position, the clip 1010 (e.g., the same clip 1010 or, in other embodiments, another clip) may be attached to the body 1001 proximate (e.g., at and/or in the recess 1007) and engage with the handle 506 to secure the handle 506 and the anchor cannula 1004. For example, the clip 1010 may retain the handle 506 and the anchor cannula 1004 (e.g., by interfering with movement of the handle 506)

and prevent the handle 506 and the anchor cannula 1004 from sliding relative to the body 1001 of anchor deployment device 1000.

The clip 1010 may be selectively coupled between locking positions in order to move between the medical device locking position and the handle locking position. For example, when the clip 1010 is engaged with a rear portion of the body 1001 and securing the medical device 102, the handle 506 and the anchor cannula 1004 are able to move relative to the body 1001. Similarly, when the clip 1010 is engaged with a central portion of the body 1001 at the recess 1007 and is restricting the handle 506 and the anchor cannula 1004 from moving relative to the body 1001, the anchor deployment device 1000 is able to move (e.g., slide) along the medical device 102. Such a configuration may enable the anchor deployment device 1000 to be secured to the medical device 102 while an anchor element is being deployed and, likewise, secure the anchor deployment device 1000 from any unwanted movement of the anchor cannula 1004 relative to the deployment cannula 1002 when the anchor deployment device 1000 is being moved and positioned along the medical device 102.

Figure 20:
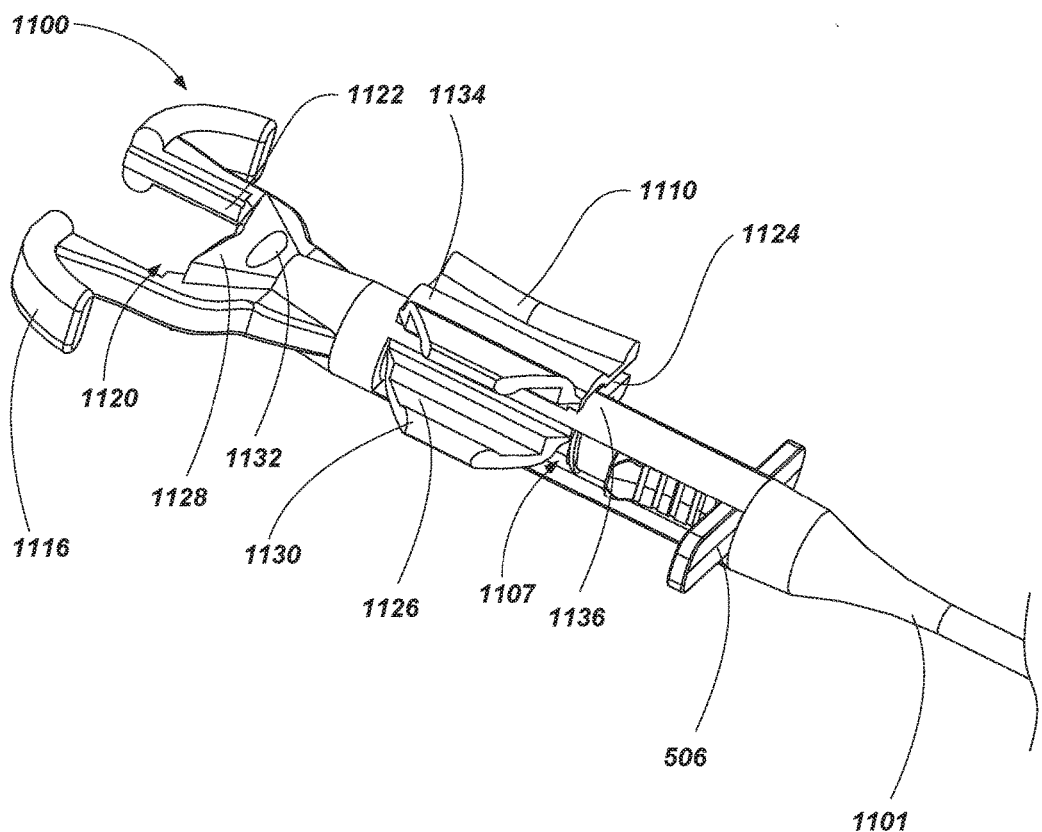
FIG. 20 depicts a perspective view of an anchor deployment device in accordance with an embodiment of the disclosure.

FIG. 20 depicts a perspective view of an anchor deployment device 1100. The anchor deployment device 1100 may be substantially similar to the anchor deployment device 1000 discussed above with reference to FIGS. 18 and 19. As shown in FIG. 20, the anchor deployment device 1100 includes at least one clip (e.g., clip 1110). For example, the clip 1110 may be configured to be positioned between a medical device locking position (see, e.g., FIG. 18) and a handle locking position (e.g., as depicted in FIG. 20).

In the medical device locking position, the clip 1110 may be coupled to a complementary portion of the body 1101 (e.g., opening 1120 positioned between rear handle 1116) to hold (e.g., lock, clamp, etc.) the medical device 102 (see, e.g., FIG. 18). For example, the clip 1110 may include channels 1124 (e.g., defined on opposing sides of the clip 1110) that receive one or more rails 1122 defined by the body 1101 on one or more sides of the opening 1120 (e.g., opposing sides of the opening 1120). The clip 1110 may include a first receiving portion 1126 having a recess or indent that is complementary to a portion of the body 1101 proximate the rear handle 1116 (e.g., protrusion 1128). A lip 1130 on the outer portion of the clip 1110 proximate the first receiving portion 1126 may act to secure the clip 1110 to the protrusion 1128 on the body 1101 in a rear position on the anchor deployment device 1100 (e.g., in the medical device locking position). For example, the lip 1130 may be received in a complementary recess 1132 or indentation in the body 1101.

In the handle locking position, the clip 1110 (e.g., the same clip 1110 or, in other embodiments, another clip) may be attached to the body 1101 proximate (e.g., at and/or in the recess 1107) and engage with the handle 506 to secure the handle 506 and the anchor cannula 1004 (see, e.g., FIG. 18). For example, a second receiving portion 1134 of the clip 1110 having a recess or indent that is complementary to a portion of the body 1101 (e.g., an upper portion 1136 of the body 1101 defining one side of the recess 1107) may engage with the body 1101 to retain the handle 506 and the anchor cannula 1104 (e.g., by interfering with movement of the handle 506) and prevent the handle 506 and the anchor cannula 1104 from sliding relative to the body 1101 of anchor deployment device 1100. As depicted, when placed the handle locking position, the clip 1110 may extend from the body 1101 in a lateral direction (e.g., in a horizontal direction).

In some embodiments, at least a portion of the clip 1110 may be symmetrical to enable the clip 1110 to be placed on the anchor deployment device 1100 in multiple orientations. For example, as depicted in FIG. 20, an upper side of the clip 1110 may be substantially symmetrical (e.g., identical) to a lower side of the clip 1110 to enable the clip 1110 to be coupled to the anchor deployment device 1100 in the orientation shown and, in substantially the same manner, in another orientation with the clip 1110 rotated 180 degrees (e.g., flipped).

Figure 21:
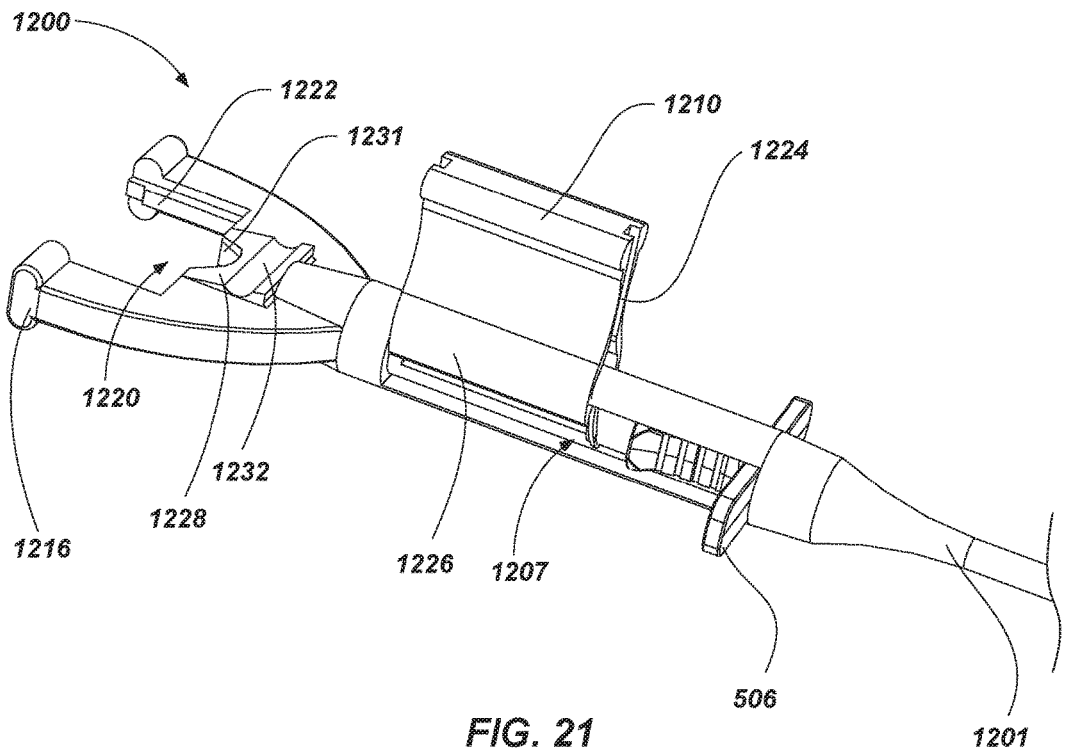
FIGS. 21 and 22 depict a perspective view and a cross-sectional side view, respectively, of an anchor deployment device in accordance with an embodiment of the disclosure.
Figure 22:
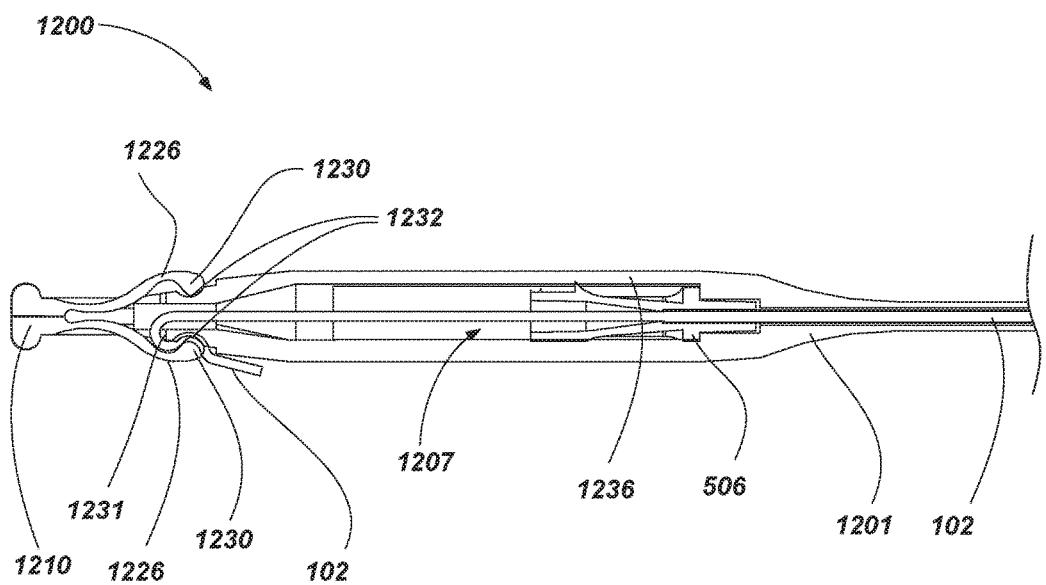

FIGS. 21 and 22 depict a perspective view and a partial cross-sectional side view, respectively, of an anchor deployment device 1200. The anchor deployment device 1200 may be substantially similar to the anchor deployment devices 1000, 1100 discussed above with reference to FIGS. 18 through 20. As shown in FIGS. 21 and 22, the anchor deployment device 1200 includes at least one clip (e.g., clip 1210). For example, the clip 1210 may be configured to be positioned between a medical device locking position (e.g., as depicted in FIG. 22) and a handle locking position (e.g., as depicted in FIG. 21).

In the medical device locking position, the clip 1210 may be coupled to a complementary portion of the body 1201 (e.g., opening 1220 positioned between rear handle 1216) to hold (e.g., lock, clamp, etc.) the medical device 102 (see FIG. 21). For example, the clip 1210 may include channels 1224 (e.g., defined on opposing sides of the clip 1210) that receive one or more rails 1222 (defined by the body 1201 on one or more sides of the opening 1220 (e.g., opposing sides of the opening 1220). The clip 1210 may include a receiving portion 1226 having a recess or indent that is complementary to a portion of the body 1201 proximate the rear handle 1216 (e.g., protrusion 1228). The receiving portion 1226 may enable the clip 1210 to couple to the body 1201 in both the medical device locking position (e.g., as depicted in FIG. 22) and the handle locking position (e.g., as depicted in FIG. 21). A lip 1230 on the outer portion of the clip 1210 proximate the receiving portion 1226 may act to secure the clip 1210 to the protrusion 1228 on the body 1201 in a rear position on the anchor deployment device 1200 (e.g., in the medical device locking position). For example, the lip 1230 may be received in a complementary recess 1232 or indentation in the body 1201.

As best shown in FIG. 22, in the medical device locking position, the medical device 102 may extend from the interior of the body 1201 through recess 1231 formed in the body 1201 and around the protrusion 1228 and the recess 1232. The clip 1210 may retain (e.g., pin, trap, etc.) between a portion of the clip 1210 (e.g., the lip 1230) and the body 1201 to secure the medical device 102.

In the handle locking position, the clip 1210 (e.g., the same clip 1210 or, in other embodiments, another clip) may be attached to the body 1201 proximate (e.g., at and/or in the recess 1207) and engage with the handle 506 to secure the handle 506 and the anchor cannula 1004 (see, e.g., FIG. 18). For example, the receiving portion 1226 of the clip 1210 having a recess or indent that is complementary to a portion of the body 1201 (e.g., an upper portion 1236 of the body 1201 defining one side of the recess 1207) may engage with the body 1201 to retain the handle 506 and the anchor cannula 1204 (e.g., by interfering with movement of the handle 506) and prevent the handle 506 and the anchor cannula 1204 from sliding relative to the body 1201 of anchor deployment device 1200. As depicted, when placed the handle locking position, the clip 1210 may extend from the body 1201 in a lateral direction (e.g., in a vertical direction).

In some embodiments, at least a portion of the clip 1210 may be symmetrical to enable the clip 1210 to be placed on the anchor deployment device 1200 in multiple orientations. For example, as depicted in FIG. 22, the upper side of the clip 1210 may be substantially symmetrical (e.g., identical) to a lower side of the clip 1210 to enable the clip 1210 to be coupled to the anchor deployment device 1200 in the orientation shown and, in substantially the same manner, in another orientation with the clip 1210 rotated 180 degrees (e.g., flipped).

Referring to FIGS. 1 through 22, in operation, a lumen of an anchor element (e.g., lumen 101, 201, 401 of anchor element 100, 200, 400) is enlarged to position the anchor element 100, 200, 400 on the anchor cannula 304 of the anchor deployment device 300. A medical device 102 (e.g., a medical device that has already been inserted and positioned within a subject) is positioned within the anchor element 302 and the anchor deployment device 300 and anchor element 100, 200, 400 are moved along the medical device 102 to position the anchor element 100, 200, 400 within the subject. The anchor element 100, 200, 400 may then be deployed within the subject utilizing the anchor deployment device (e.g., one of anchor deployment devices 300, 500, 600, 700, 800, 900, 1000, 1100, 1200) to deploy the lobes 104, 204, 404 of the anchor element 100, 200, 400 and to force the anchor element 100, 200, 400 onto (e.g., about, around) the medical device 102 with a deployment cannula. Constriction of the anchor element 100, 200, 400 about the medical device 102 as the anchor element 100, 200, 400 contracts toward the initial lumen size of the anchor element 100, 200, 400 acts to secure the anchor element 100, 200, 400 about the medical device 102 while both the anchor element 100, 200, 400 and the medical device 102 are positioned within the subject. For example, the anchor element 100, 200, 400 may contract to the initial size of the lumen 101, 201, 401 of the anchor element 100, 200, 400 or to a cross-sectional area between the initial size and the enlarged (e.g., deformed) size of the lumen 101, 201, 401 of the anchor element 100, 200, 400. In some embodiments, the constriction of the anchor element 100, 200, 400 may also constrict or compress a portion of the medical device 102 (e.g., a cannula).

Once the anchor element 100, 200, 400 is placed over the medical device 102 within the subject, the lobes 104, 204, 404 of the anchor element 100, 200, 400 may anchor the medical device 102 by engaging with one or more portions of the subject's tissue to at least partially retain the medical device 102 in a desired position within the subject.

In some embodiments, a loading device may be utilized to load one or more anchor elements (e.g., anchor elements 100, 200, 400) onto a portion (e.g., an anchor cannula) of the anchor deployment device (e.g., one of anchor deployment devices 300, 500, 600, 700, 800, 900, 1000, 1100, 1200).

Figure 23:
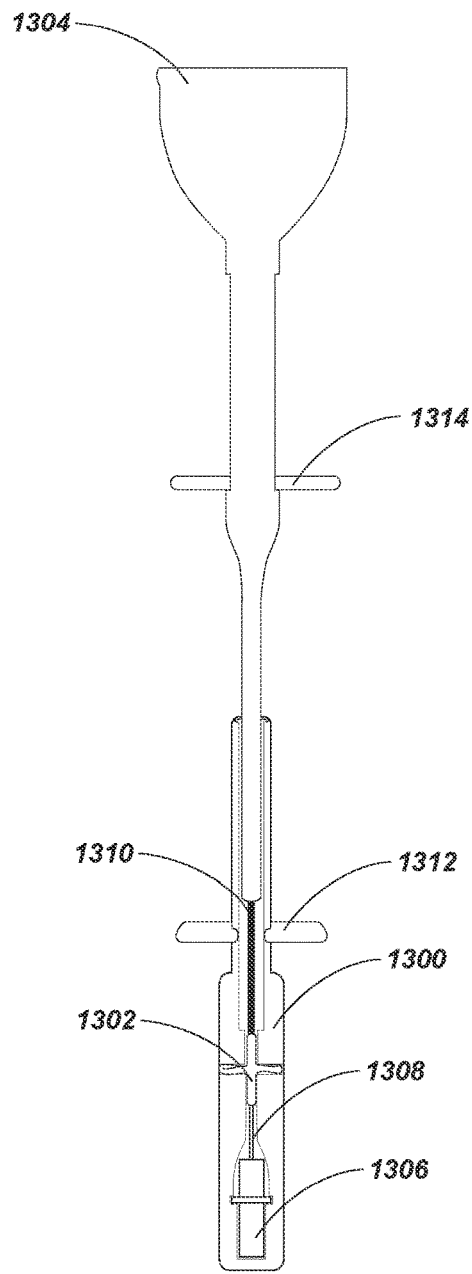
FIGS. 23 and 24 depict assemblies including an anchor deployment device and an anchor loading device in accordance with embodiments of the disclosure.

For example, FIG. 23 depicts an anchor loading device 1300 loading an anchor element 1302 (e.g., which may be similar or the same as one of anchor elements 100, 200, 400) onto an anchor deployment device 1304 (e.g., which may be similar or the same as one of anchor deployment devices 300, 500, 600, 700, 800, 900, 1000, 1100, 1200). As depicted, the anchor loading device 1300 may include a base 1306 having a post 1308 extending from the base 1306. The post 1308 may have the anchor element 1302 mounted on the post 1308 (e.g., by sliding the anchor element 1302 over the post 1308 and positioning the anchor element 1302 in the deployed position). In some embodiments, the post 1308 (e.g., and the base 1306) may be removably connected to the anchor loading device 1300 to facilitate loading of the anchor element 1302 on the post 1308.

The anchor loading device 1300 may have openings therein for receiving one or more of the anchor element 1302 and a portion of the anchor deployment device 1304.

As shown in FIG. 23, a cannula 1310 of the anchor deployment device 1304 may be paced adjacent to the anchor element 1302 (e.g., by receiving a portion of the post 1308 within an inner channel of a cannula 1310 of the anchor deployment device 1304). For example, the post 1308 may have a thickness (e.g., diameter) less than the inner channel of a cannula 1310 of the anchor deployment device 1304 to enable the cannula 1310 to be received on the post 1308. In other embodiments, the post 1308 may have a thickness (e.g., diameter) greater than a thickness (e.g., diameter) of the cannula 1310 of the anchor deployment device 1304 and the post 1308 may be received over the cannula 1310.

The anchor element 1302 may be transferred from the post 1308 to the cannula 1310 of the anchor deployment device 1304 to load the anchor element 1302 on the anchor deployment device 1304 for installation on a medical device, as discussed above. For example, force may be applied between the anchor deployment device 1304 and the anchor loading device 1300 to transfer the anchor element 1302 from the post 1308 to the cannula 1310. As depicted, a user may apply force (e.g., with the user's hands or fingers) to the anchor loading device 1300 (e.g., at one or more handles 1312) and to the anchor deployment device 1304 (e.g., at one or more handles 1314) to transfer (e.g., force) the anchor element 1302 from the post 1308 to the cannula 1310.

Figure 24:
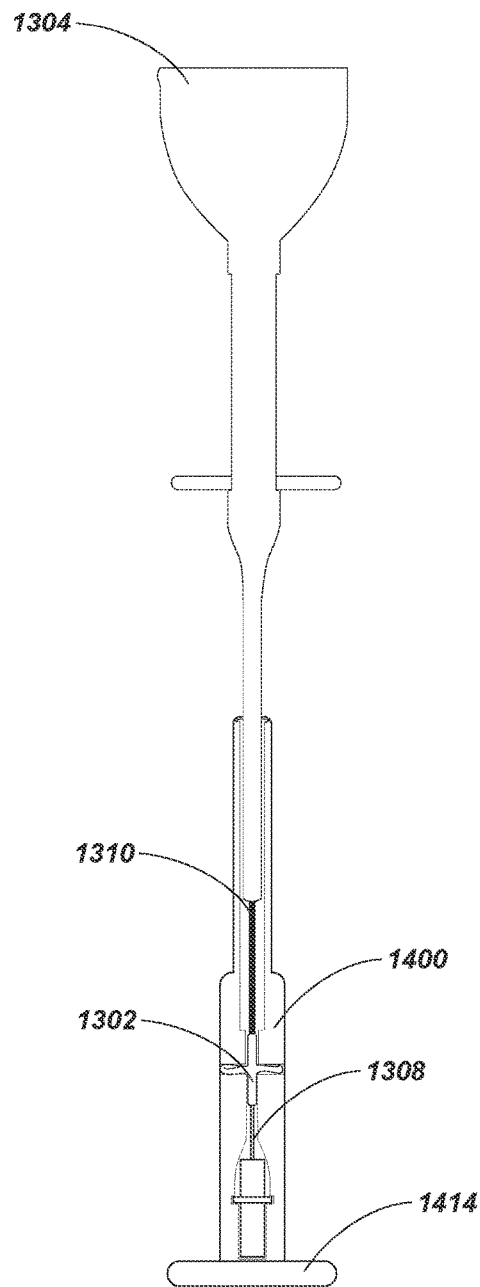

FIG. 24 depicts an anchor loading device 1400 that may be similar to the anchor loading device 1300 discussed above in relation to FIG. 23. However, as depicted, the anchor loading device 1400 may include an enlarged base portion 1414 that enables the anchor loading device 1400 to be positioned on or against an object (e.g., a table, a wall) to provide a force to the anchor loading device 1400 when the anchor element 1302 is transferred from the post 1308 to the cannula 1310 of the anchor deployment device 1304.

In some embodiments, an anchor loading device may be configured to apply a force between the anchor deployment device and the anchor loading device to transfer the anchor element from the post to the cannula by other mechanisms. For example, the anchor loading device may include a rotating portion that converts rotational force to linear movement (e.g., a worm drive), a lever system, etc. that provides a mechanical advantage in order to force the anchor element from the post to the cannula.

Figure 25:
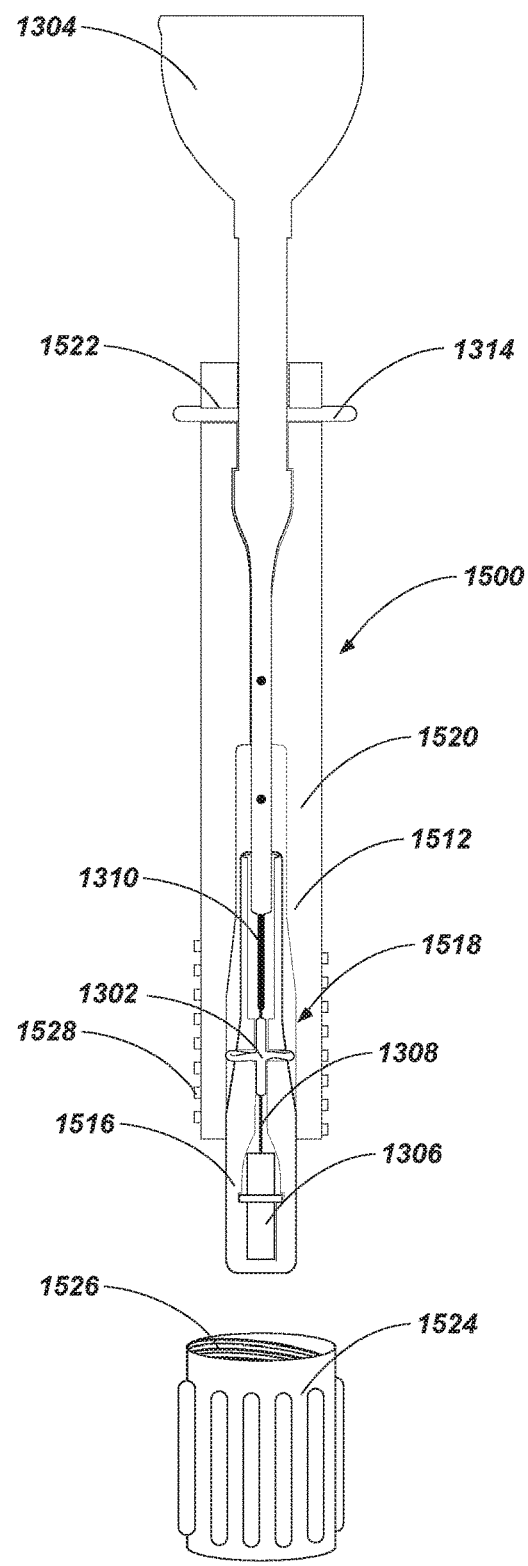
FIG. 25 depicts an exploded, partial cross-sectional view of an assembly including an anchor deployment device and an anchor loading device in accordance with embodiments of the disclosure.

For example, FIG. 25 depicts an exploded, partial cross-sectional view of an anchor loading device 1500 (e.g., which may be similar and include one or more components of anchor loading devices 1300, 1400) loading an anchor element 1302 (e.g., which may be similar or the same as one of anchor elements 100, 200, 400) onto an anchor deployment device 1304 (e.g., which may be similar or the same as one of anchor deployment devices 300, 500, 600, 700, 800, 900, 1000, 1100, 1200). As depicted, the anchor loading device 1500 may include the base 1306 having the post 1308 extending from the base 1306. The base 1306 and post 1308 may be at least partially housed in an inner member 1516 of the anchor loading device 1500. Inner member 1516 may be at least partially received within a cavity 1518 in an outer member 1520 of the anchor loading device 1500 and may move relative to the outer member 1520 within the cavity 1518 of the outer member 1520. For example, the inner member 1516 may translate along a longitudinal axis of the outer member 1520 or the anchor loading device 1500 within the cavity 1518.

The post 1308 may have the anchor element 1302 mounted on the post 1308 (e.g., by sliding the anchor element 1302 over the post 1308 and positioning the anchor element 1302 in the deployed position within openings provided in the inner member 1516). In some embodiments, the post 1308 (e.g., and the base 1306) may be removably connected to the anchor loading device 1500 to facilitate loading of the anchor element 1302 on the post 1308.

The anchor loading device 1500 may have openings therein for receiving one or more of the anchor element 1302 and a portion of the anchor deployment device 1304.

As shown in FIG. 25, a cannula 1310 of the anchor deployment device 1304 may be paced adjacent to the anchor element 1302 (e.g., by receiving a portion of the post 1308 within an inner channel of the cannula 1310 of the anchor deployment device 1304). For example, the post 1308 may have a thickness (e.g., diameter) less than the inner channel of a cannula 1310 of the anchor deployment device 1304 to enable the cannula 1310 to be received on the post 1308. In other embodiments, the post 1308 may have a thickness (e.g., diameter) greater than a thickness (e.g., diameter) of the cannula 1310 of the anchor deployment device 1304 and the post 1308 may be received over the cannula 1310.

The anchor element 1302 may be transferred, with the anchor loading device 1500, from the post 1308 to the cannula 1310 of the anchor deployment device 1304 to load the anchor element 1302 on the anchor deployment device 1304 for installation on a medical device, as discussed above. For example, force may be applied between the anchor deployment device 1304 and the anchor loading device 1500 to transfer the anchor element 1302 from the post 1308 to the cannula 1310. As depicted, the anchor deployment device 1304 may be secured to (e.g., within a portion of) the anchor loading device 1500 to hold the anchor deployment device 1304 in a fixed position relative to a portion of the anchor loading device 1500 (e.g., the outer member 1520). For example, a portion of the anchor deployment device 1304 (e.g., one or more of the handles 1314) may be placed within corresponding apertures 1522 in the outer member 1520.

The anchor element 1302 may be transferred (e.g., forced) from the post 1308 to the cannula 1310 by the anchor loading device 1500 by moving (e.g., translating) the inner member 1516 relative to the outer member 1520 (e.g., and the anchor deployment device 1304 which is fixed relative to the outer member 1520). For example, the anchor loading device 1500 may include a rotational member 1524 having threads 1526 (e.g., inner threads) that engage with complementary threads 1528 (e.g., outer threads) on the outer member 1520. A portion of the rotation member 1524 may engage (e.g., abut) a portion of the inner member 1516 (e.g., an end of the inner member 1516) and force the inner member 1516 within the cavity 1518 in a linear direction as the rotational member 1524 is threaded onto the outer member 1520. In such an embodiment, the force applied to the anchor loading device 1500 by rotating the rotational member 1524 is applied to the inner member 1516 to translate the inner member 1516 toward and into the cavity 1518 in the outer member 1520 in order to force the anchor element 1302 from the post 1308 to the cannula 1310.

Once being apprised of the instant disclosure, one of ordinary skill in the art will be able to make and use the devices and assemblies disclosed herein. For example, the anchor elements may be formed from a polymer (e.g., a polyurethane such as CARBOTHANE®) and springs may be formed from a metal material (e.g., 316 stainless steel).

What is claimed is:

1. An anchor deployment device comprising at least one cannula configured to receive at least one anchor element on the at least one cannula and a medical device within the at least one cannula, the anchor deployment device configured to secure a main body of the anchor deployment device to at least a portion of the medical device, wherein the anchor deployment device further comprises a locking mechanism configured to secure the medical device to the anchor deployment device, the locking mechanism comprising at least one removable clip that is removable from the main body of the anchor deployment device, wherein, when the at least one removable clip is coupled to the main body of the anchor deployment device in a first position, the at least one removable clip is configured to be engaged with the medical device and disengaged from a hub of the at least one cannula, when the at least one removable clip is coupled to the main body of the anchor deployment device in a second position, the at least one removable clip is configured to be disengaged from the medical device and engaged with the huh, wherein the at least one cannula of the anchor deployment device comprises:
   a first cannula configured to receive the at least one anchor element thereon; and
   a second cannula having at least a portion of the first cannula received therein,
wherein the first cannula, is movable relative to the second cannula, and wherein the second cannula is configured to force the at least one anchor element off of the first cannula in order to secure the anchor deployment device to the at least a portion of the medical device.

2. The anchor deployment device of claim 1, wherein the first cannula comprises the hub movably received within a portion of the anchor deployment device such that movement of the hub translates the first cannula relative to the second cannula.

3. The anchor deployment device of claim 2, wherein the at least one removable clip is configured to secure the hub to restrict movement of the hub and the first cannula relative to the second cannula.

4. The anchor deployment device of claim 1, wherein the at least one removable clip comprises a single clip that is configured to be positioned in both the first position and the second position.

5. An anchor deployment device, comprising: at least one cannula configured to receive at least one anchor element on the at least one cannula and a medical device within the at least one cannula; and a locking mechanism configured to selectively secure the medical device and a portion of the at least one cannula, wherein the locking mechanism comprises a removable clip that is removable from a main body of the anchor deployment device, wherein, when the removable clip is coupled to the main body of the anchor deployment device in a first position, the removable clip is configured to be engaged with the medical device and disengaged from the portion of the at least one cannula and, when the removable clip is coupled to the main body of the anchor deployment device in a second position, the removable clip is configured to be disengaged from the medical device and engaged with the portion of the at least one cannula, wherein the at least one cannula of the anchor deployment device comprises:
   a first cannula configured to receive the at least one anchor element thereon; and a second cannula having at least a portion of the first cannula received therein, wherein the first cannula is movable relative to the second cannula, and wherein the second cannula is configured to force the at least one anchor element off of the first cannula in order to secure the anchor deployment device to the at least a portion of the medical device.

6. An anchor deployment device assembly comprising:
the anchor deployment device of claim 1 configured to position the at least one anchor element on the medical device to secure a portion of the medical device within a subject; and
an anchor loading device comprising at least one post to receive the at least one anchor element, wherein the anchor loading device is configured to transfer the at least one anchor element from the anchor loading device to the anchor deployment device when a force is applied to at least one of the anchor loading device or the anchor deployment device.

7. The anchor deployment device assembly of claim 6, wherein the anchor loading device is configured to transfer the at least one anchor element from a post of the anchor loading device onto the cannula of the anchor deployment device when a force is applied between the anchor loading device and the anchor deployment device.

8. The anchor deployment device assembly of claim 7, wherein the anchor loading device comprises a rotational member configured to transfer the at least one anchor element from the post of the anchor loading device onto the cannula of the anchor deployment device by translating a portion of the anchor loading device relative to the anchor deployment device.

9. A method of operating a deployment device, the method comprising:
securing a medical device positioned at least partially within the at least one cannula of the deployment device of claim 1 with the locking mechanism comprising the at least one removable clip in the first position;
releasing the medical device; and
removing the locking mechanism from the first position on the deployment device to release the medical device and positioning the clip at Hall the second position on the deployment device to secure the at least a portion of the at least one cannula of the deployment device with the locking mechanism.

* * * * *

UNITED STATES PATENT AND TRADEMARK OFFICE
CERTIFICATE OF CORRECTION

PATENT NO.        : 10,448,972 B2
APPLICATION NO.   : 15/759492
DATED             : October 22, 2019
INVENTOR(S)       : N. Sandor Racz, James Shoemake and Kevin Dean Joiner Page 1 of 1

It is certified that error appears in the above-identified patent and that said Letters Patent is hereby corrected as shown below:

In the Specification

| | | |
|---|---|---|
| Column 15, | Line 61, | change "cannula 1104" to --cannula 1004-- |
| Column 15, | Line 63, | change "cannula 1104" to --cannula 1004-- |
| Column 16, | Line 61, | change "cannula 1204" to --cannula 1004-- |
| Column 16, | Line 63, | change "cannula 1204" to --cannula 1004-- |
| Column 17, | Line 19, | change "element 302" to --cannula 304-- |

In the Claims

| | | | |
|---|---|---|---|
| Claim 1, | Column 20, | Line 24, | change "huh, wherein" to --hub, wherein-- |
| Claim 9, | Column 22, | Line 20, | change "positioning the clip" to --positioning the removable clip-- |
| Claim 9, | Column 22, | Line 20, | change "at Hall the second" to --at the second-- |

Signed and Sealed this
Third Day of December, 2019

Andrei Iancu
*Director of the United States Patent and Trademark Office*